(12) United States Patent
Tinkham et al.

(10) Patent No.: US 8,480,570 B2
(45) Date of Patent: Jul. 9, 2013

(54) ENDOSCOPE CAP

(75) Inventors: Brian Tinkham, South Boston, MA (US); Douglas Pleskow, Needham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1142 days.

(21) Appl. No.: 12/029,148

(22) Filed: Feb. 11, 2008

(65) Prior Publication Data

US 2008/0194913 A1      Aug. 14, 2008

Related U.S. Application Data

(60) Provisional application No. 60/889,444, filed on Feb. 12, 2007.

(51) Int. Cl.
*A61B 1/00* (2006.01)
*A61M 5/178* (2006.01)

(52) U.S. Cl.
USPC .................. 600/154; 600/104; 604/167.04

(58) Field of Classification Search
USPC .................. 600/154, 104; 604/167.04, 95.04, 604/537, 167.01–167.03, 167.06
See application file for complete search history.

(56) References Cited

U.S. PATENT DOCUMENTS

| | | | |
|---|---|---|---|
| 561,059 A | 5/1896 | Mitchell et al. | |
| 1,204,053 A | 11/1916 | Moore | |
| 1,213,001 A | 1/1917 | Philips | |
| 1,901,731 A | 3/1933 | Buerger | |
| 2,623,520 A | 12/1952 | Bamford, Jr. et al. | |
| 3,015,869 A | 1/1962 | Rapata | |
| 3,536,281 A | 10/1970 | Meehan et al. | |
| 3,602,228 A | 8/1971 | Cowley | |
| 3,677,243 A | 7/1972 | Nerz | |
| 4,178,920 A | 12/1979 | Cawood, Jr. et al. | |
| 4,198,958 A | 4/1980 | Utsugi | |
| 4,240,411 A | 12/1980 | Hosono | |
| 4,306,562 A | 12/1981 | Osborne | |
| 4,326,516 A | 4/1982 | Schultz et al. | |
| 4,345,606 A | 8/1982 | Littleford | |

(Continued)

FOREIGN PATENT DOCUMENTS

DE    41 15 007 A1    11/1992
DE    199 11 911 A1    9/1999

(Continued)

OTHER PUBLICATIONS

Arndorfer Inc. Information Sheet, dated on or before Mar. 6, 2000, 7 sheets.

(Continued)

*Primary Examiner* — Anhtuan T. Nguyen
*Assistant Examiner* — Alireza Nia
(74) *Attorney, Agent, or Firm* — Seager, Tufte & Wickhem LLC

(57) ABSTRACT

A cap including an outer shell configured to be coupled to an access port of an endoscope, and a resilient member positioned interior of the inner peripheral surface of the outer shell. The resilient member includes an upper surface, a lower surface, an outer peripheral surface and a central opening sized to accommodate an endoscopic instrument therethrough. The resilient member further includes a slit extending outward from the circumferential surface of the central opening toward the outer peripheral surface of the resilient member.

14 Claims, 17 Drawing Sheets

U.S. PATENT DOCUMENTS

| | | | |
|---|---|---|---|
| 4,367,905 A | 1/1983 | Nauta | |
| 4,411,654 A | 10/1983 | Boarini et al. | |
| 4,412,832 A | 11/1983 | Kling et al. | |
| 4,474,174 A | 10/1984 | Petruzzi | |
| RE31,855 E | 3/1985 | Osborne | |
| 4,509,944 A | 4/1985 | King et al. | |
| 4,609,370 A | 9/1986 | Morrison | |
| 4,611,594 A | 9/1986 | Grayhack et al. | |
| 4,653,477 A | 3/1987 | Akui et al. | |
| 4,687,470 A | 8/1987 | Okada | |
| 4,696,668 A | 9/1987 | Wilcox | |
| 4,700,694 A | 10/1987 | Shishido | |
| 4,715,360 A | 12/1987 | Akui et al. | |
| 4,723,942 A | 2/1988 | Scott | |
| 4,738,666 A | 4/1988 | Fuqua | |
| 4,748,982 A | 6/1988 | Horzewski et al. | |
| 4,762,129 A | 8/1988 | Bonzel | |
| 4,771,777 A | 9/1988 | Horzewski et al. | |
| 4,781,677 A | 11/1988 | Wilcox | |
| 4,787,884 A | 11/1988 | Goldberg | |
| D301,365 S | 5/1989 | Gette | |
| 4,835,824 A | 6/1989 | Durham et al. | |
| 4,844,092 A | 7/1989 | Rydell et al. | |
| 4,858,810 A | 8/1989 | Intlekofer et al. | |
| 4,867,605 A | 9/1989 | Myers et al. | |
| 4,900,184 A | 2/1990 | Cleveland | |
| 4,905,667 A | 3/1990 | Foerster et al. | |
| 4,917,103 A | 4/1990 | Gambale et al. | |
| 4,920,953 A | 5/1990 | McGown | |
| 4,927,418 A | 5/1990 | Dake et al. | |
| 4,928,669 A | 5/1990 | Sullivan | |
| 4,928,693 A | 5/1990 | Goodin et al. | |
| 4,932,413 A | 6/1990 | Shockey et al. | |
| 4,940,062 A | 7/1990 | Hampton et al. | |
| 4,946,443 A | 8/1990 | Hauser et al. | |
| 4,973,329 A | 11/1990 | Park et al. | |
| 4,983,168 A | 1/1991 | Moorehead | |
| 4,988,356 A | 1/1991 | Crittenden et al. | |
| 4,995,872 A | 2/1991 | Ferrara | |
| 4,997,421 A | 3/1991 | Palsrok et al. | |
| 5,000,745 A * | 3/1991 | Guest et al. | 604/256 |
| 5,026,366 A | 6/1991 | Leckrone | |
| 5,034,001 A | 7/1991 | Garrison et al. | |
| 5,040,548 A | 8/1991 | Yock | |
| 5,059,186 A * | 10/1991 | Yamamoto et al. | 604/537 |
| 5,061,273 A | 10/1991 | Yock | |
| 5,064,414 A | 11/1991 | Revane | |
| 5,098,064 A | 3/1992 | Daly et al. | |
| 5,106,054 A | 4/1992 | Mollenauer et al. | |
| 5,125,915 A | 6/1992 | Berry et al. | |
| 5,127,393 A | 7/1992 | McFarlin et al. | |
| 5,127,626 A | 7/1992 | Hilal et al. | |
| 5,135,535 A | 8/1992 | Kramer | |
| 5,137,288 A | 8/1992 | Starkey et al. | |
| 5,137,517 A | 8/1992 | Loney et al. | |
| 5,139,032 A | 8/1992 | Jahrmarkt et al. | |
| 5,147,305 A | 9/1992 | Nakamura et al. | |
| 5,147,377 A | 9/1992 | Sahota | |
| 5,154,725 A | 10/1992 | Leopold | |
| 5,158,545 A | 10/1992 | Trudell et al. | |
| 5,160,323 A | 11/1992 | Andrew | |
| 5,161,534 A | 11/1992 | Berthiaume | |
| 5,163,941 A | 11/1992 | Garth et al. | |
| 5,167,634 A | 12/1992 | Corrigan, Jr. et al. | |
| 5,167,636 A | 12/1992 | Clement | |
| 5,171,222 A | 12/1992 | Euteneuer et al. | |
| 5,180,367 A | 1/1993 | Kontos et al. | |
| 5,191,888 A | 3/1993 | Palmer et al. | |
| 5,195,978 A | 3/1993 | Schiffer | |
| 5,199,948 A | 4/1993 | McPhee | |
| 5,205,822 A | 4/1993 | Johnson et al. | |
| 5,219,332 A | 6/1993 | Nelson et al. | |
| 5,219,335 A | 6/1993 | Willard et al. | |
| 5,232,445 A | 8/1993 | Bonzel | |
| 5,242,389 A | 9/1993 | Schrader et al. | |
| 5,248,306 A | 9/1993 | Clark et al. | |
| 5,250,033 A | 10/1993 | Evans et al. | |
| 5,259,366 A | 11/1993 | Reydel et al. | |
| 5,263,932 A | 11/1993 | Jang | |
| 5,267,958 A | 12/1993 | Buchbinder et al. | |
| 5,279,562 A | 1/1994 | Sirhan et al. | |
| 5,281,203 A | 1/1994 | Ressemann | |
| 5,282,479 A | 2/1994 | Havran | |
| 5,290,232 A | 3/1994 | Johnson et al. | |
| 5,290,241 A | 3/1994 | Kraus et al. | |
| 5,300,085 A | 4/1994 | Yock | |
| 5,304,143 A | 4/1994 | Green et al. | |
| 5,306,247 A | 4/1994 | Pfenninger | |
| 5,308,318 A | 5/1994 | Plassche, Jr. | |
| 5,314,408 A | 5/1994 | Salmon et al. | |
| 5,320,602 A | 6/1994 | Karpiel | |
| 5,324,259 A | 6/1994 | Taylor et al. | |
| 5,324,269 A | 6/1994 | Miraki | |
| 5,328,472 A | 7/1994 | Steinke et al. | |
| 5,334,143 A | 8/1994 | Carroll | |
| 5,334,147 A | 8/1994 | Johnson | |
| 5,334,187 A | 8/1994 | Fischell et al. | |
| 5,336,184 A | 8/1994 | Teirstein | |
| 5,338,313 A | 8/1994 | Mollenauer et al. | |
| 5,342,297 A | 8/1994 | Jang | |
| 5,350,395 A | 9/1994 | Yock | |
| 5,352,215 A | 10/1994 | Thome et al. | |
| 5,354,280 A | 10/1994 | Haber et al. | |
| 5,357,978 A | 10/1994 | Turk | |
| 5,364,355 A | 11/1994 | Alden et al. | |
| 5,364,376 A | 11/1994 | Horzewski et al. | |
| 5,368,567 A | 11/1994 | Lee | |
| 5,370,623 A | 12/1994 | Kreamer | |
| 5,380,283 A | 1/1995 | Johnson | |
| 5,385,552 A | 1/1995 | Haber et al. | |
| 5,387,226 A | 2/1995 | Miraki | |
| 5,389,087 A | 2/1995 | Miraki | |
| 5,391,153 A | 2/1995 | Haber et al. | |
| 5,395,335 A | 3/1995 | Jang | |
| 5,395,342 A | 3/1995 | Yoon | |
| 5,397,302 A | 3/1995 | Weaver et al. | |
| 5,397,335 A | 3/1995 | Gresl et al. | |
| 5,407,433 A | 4/1995 | Loomas | |
| 5,409,459 A | 4/1995 | Gambale | |
| 5,413,559 A | 5/1995 | Sirhan et al. | |
| 5,415,639 A | 5/1995 | VandenEinde et al. | |
| 5,441,486 A | 8/1995 | Yoon | |
| 5,448,993 A | 9/1995 | Lynch et al. | |
| 5,449,363 A | 9/1995 | Brust et al. | |
| 5,451,233 A | 9/1995 | Yock | |
| 5,454,790 A | 10/1995 | Dubrul | |
| 5,458,584 A | 10/1995 | Ginn et al. | |
| 5,458,605 A | 10/1995 | Klemm | |
| 5,460,168 A | 10/1995 | Masubuchi et al. | |
| 5,462,530 A | 10/1995 | Jang | |
| 5,480,389 A | 1/1996 | McWha et al. | |
| 5,489,271 A | 2/1996 | Andersen | |
| 5,490,837 A | 2/1996 | Blaeser et al. | |
| 5,496,346 A | 3/1996 | Horzewski et al. | |
| 5,501,227 A | 3/1996 | Yock | |
| 5,531,700 A | 7/1996 | Moore et al. | |
| 5,536,234 A | 7/1996 | Newman | |
| 5,536,248 A | 7/1996 | Weaver et al. | |
| 5,540,236 A | 7/1996 | Ginn | |
| 5,547,469 A | 8/1996 | Rowland et al. | |
| 5,599,299 A | 2/1997 | Weaver et al. | |
| 5,599,300 A | 2/1997 | Weaver et al. | |
| 5,599,305 A * | 2/1997 | Hermann et al. | 604/95.04 |
| 5,613,949 A | 3/1997 | Miraki | |
| 5,626,600 A | 5/1997 | Horzewski et al. | |
| 5,634,475 A | 6/1997 | Wolvek | |
| 5,637,086 A | 6/1997 | Ferguson et al. | |
| 5,685,853 A | 11/1997 | Bonnet | |
| 5,693,015 A | 12/1997 | Walker et al. | |
| 5,706,827 A | 1/1998 | Ehr et al. | |
| 5,707,363 A | 1/1998 | Crawford et al. | |
| 5,709,658 A | 1/1998 | Sirhan et al. | |
| 5,718,680 A | 2/1998 | Kraus et al. | |
| 5,720,759 A | 2/1998 | Green et al. | |
| 5,725,504 A | 3/1998 | Collins | |
| 5,765,682 A | 6/1998 | Bley | |
| 5,788,681 A | 8/1998 | Weaver et al. | |

| | | | |
|---|---|---|---|
| 5,800,414 A | 9/1998 | Cazal | |
| 5,814,026 A | 9/1998 | Yoon | |
| 5,820,600 A | 10/1998 | Carlson et al. | |
| 5,823,995 A | 10/1998 | Fitzmaurice et al. | |
| 5,833,706 A | 11/1998 | St. Germain et al. | |
| 5,836,306 A | 11/1998 | Duane et al. | |
| 5,843,028 A | 12/1998 | Weaver et al. | |
| 5,849,016 A | 12/1998 | Suhr | |
| 5,851,189 A | 12/1998 | Forber | |
| 5,891,056 A | 4/1999 | Ramzipoor | |
| 5,919,004 A | 7/1999 | Christenson | |
| 5,921,971 A | 7/1999 | Agro et al. | |
| 5,931,833 A | 8/1999 | Silverstein | |
| 5,935,114 A | 8/1999 | Jang et al. | |
| 5,978,699 A | 11/1999 | Fehse et al. | |
| 5,997,515 A | 12/1999 | de la Torre et al. | |
| 6,007,522 A | 12/1999 | Agro et al. | |
| 6,053,861 A | 4/2000 | Grossi | |
| RE36,702 E | 5/2000 | Green et al. | |
| 6,083,203 A | 7/2000 | Yoon | |
| 6,093,195 A | 7/2000 | Ouchi | |
| 6,096,009 A | 8/2000 | Windheuser et al. | |
| 6,106,487 A | 8/2000 | Duane et al. | |
| 6,117,070 A * | 9/2000 | Akiba | 600/154 |
| 6,152,910 A | 11/2000 | Agro et al. | |
| 6,190,333 B1 | 2/2001 | Valencia | |
| 6,190,358 B1 | 2/2001 | Fitzmaurice et al. | |
| 6,200,262 B1 | 3/2001 | Ouchi | |
| 6,245,437 B1 | 6/2001 | Shiiki et al. | |
| 6,254,529 B1 | 7/2001 | Ouchi | |
| 6,277,100 B1 | 8/2001 | Raulerson et al. | |
| 6,312,404 B1 | 11/2001 | Agro et al. | |
| 6,322,577 B1 | 11/2001 | McInnes | |
| 6,346,093 B1 | 2/2002 | Allman et al. | |
| 6,371,944 B1 | 4/2002 | Liu et al. | |
| 6,520,951 B1 | 2/2003 | Carrillo, Jr. et al. | |
| 6,582,401 B1 | 6/2003 | Windheuser et al. | |
| 6,606,515 B1 | 8/2003 | Windheuser et al. | |
| 6,607,529 B1 | 8/2003 | Jones et al. | |
| 6,663,597 B1 | 12/2003 | Windheuser et al. | |
| 6,663,598 B1 * | 12/2003 | Carrillo et al. | 604/167.01 |
| 6,746,442 B2 | 6/2004 | Agro et al. | |
| 6,746,466 B2 | 6/2004 | Eidenschink et al. | |
| 6,764,484 B2 | 7/2004 | Richardson et al. | |
| D498,992 S | 11/2004 | Bloom | |
| 6,827,718 B2 | 12/2004 | Hutchins et al. | |
| 6,851,424 B2 | 2/2005 | Scopton | |
| 6,863,661 B2 | 3/2005 | Carrillo, Jr. et al. | |
| 6,869,416 B2 | 3/2005 | Windheuser et al. | |
| 6,879,854 B2 | 4/2005 | Windheuser et al. | |
| 6,893,393 B2 | 5/2005 | Carrillo, Jr. | |
| 6,925,323 B2 | 8/2005 | Snoke | |
| 6,997,908 B2 | 2/2006 | Carrillo, Jr. et al. | |
| 7,009,837 B2 | 3/2006 | Lo | |
| 7,025,721 B2 | 4/2006 | Cohen et al. | |
| 7,060,052 B2 | 6/2006 | Windheuser et al. | |
| 7,076,285 B2 | 7/2006 | Windheuser et al. | |
| 7,160,283 B2 | 1/2007 | Richardson et al. | |
| 7,172,577 B2 | 2/2007 | Mangano et al. | |
| 7,178,520 B2 | 2/2007 | Scopton | |
| 7,179,252 B2 | 2/2007 | Agro et al. | |
| 7,544,193 B2 | 6/2009 | Agro et al. | |
| 7,637,863 B2 * | 12/2009 | Deal et al. | 600/104 |
| 2001/0020154 A1 | 9/2001 | Bigus et al. | |
| 2001/0029362 A1 | 10/2001 | Sirhan et al. | |
| 2001/0047135 A1 | 11/2001 | Daniels et al. | |
| 2003/0088153 A1 | 5/2003 | Carrillo, Jr. et al. | |
| 2003/0233043 A1 | 12/2003 | Windheuser et al. | |
| 2004/0106852 A1 | 6/2004 | Windheuser et al. | |
| 2004/0193142 A1 | 9/2004 | Agro et al. | |
| 2005/0059890 A1 | 3/2005 | Deal et al. | |
| 2005/0090713 A1 | 4/2005 | Gonzales et al. | |
| 2005/0090835 A1 | 4/2005 | Deal et al. | |
| 2005/0148950 A1 | 7/2005 | Windheuser et al. | |
| 2005/0165277 A1 | 7/2005 | Carrillo, Jr. et al. | |
| 2005/0171402 A1 | 8/2005 | Cohen et al. | |
| 2005/0250983 A1 | 11/2005 | Tremaglio et al. | |
| 2006/0135850 A1 | 6/2006 | Cohen et al. | |
| 2006/0142734 A1 | 6/2006 | Carrillo, Jr. et al. | |
| 2006/0229496 A1 | 10/2006 | Windheuser et al. | |
| 2006/0247523 A1 | 11/2006 | Windheuser et al. | |
| 2006/0287578 A1 | 12/2006 | Hamazaki | |

FOREIGN PATENT DOCUMENTS

| | | |
|---|---|---|
| DE | 19916866 | 10/1999 |
| EP | 0308815 | 3/1989 |
| EP | 0 328 760 A2 | 8/1989 |
| EP | 0 388 112 A2 | 9/1990 |
| EP | 0 792 657 A2 | 9/1997 |
| EP | 0 801 955 B1 | 3/1999 |
| JP | 50-108287 | 9/1975 |
| JP | 3126428 A | 5/1991 |
| JP | 6-23055 A | 2/1994 |
| JP | 7-155382 A | 6/1994 |
| JP | 9094253 | 4/1997 |
| WO | WO 92/03963 | 3/1992 |
| WO | WO 96/13296 | 5/1996 |
| WO | WO 96/33764 | 10/1996 |
| WO | WO 98/10820 | 3/1998 |
| WO | WO 98/10821 | 3/1998 |
| WO | WO 99/38557 | 8/1999 |
| WO | WO 99/59664 | 11/1999 |
| WO | WO 00/69499 | 11/2000 |
| WO | WO 00/69500 | 11/2000 |
| WO | WO 2005/107842 | 11/2005 |

OTHER PUBLICATIONS

Knecht, Gregory L., M.D. et al., "Double-Channel Fistulotome for Endoscopic Drainage of Pancreatic Pseudocyst", *Gastrointestinal Endoscopy*, vol. 37, No. 3, May/Jun. 1991, pp. 356-357.

Siegel, Jerome H., M.D. et al., "Two New Methods for Selective Bile Duct Cannulation and Sphincterotomy", *Gastrointestinal Endoscopy*, vol. 33, No. 6, Dec. 1987, pp. 438-440.

U.S. Appl. No. 12/427,438 to Carrillo, Jr. et al., filed Apr. 21, 2009.

* cited by examiner

ENDOSCOPE CAP

RELATED APPLICATIONS

This application claims the benefit of Provisional U.S. Application No. 60/889,444, filed Feb. 12, 2007, the entire disclosure of which is incorporated herein by reference.

TECHNICAL FIELD

The disclosure generally relates to a cap for an endoscope. More specifically, the disclosure pertains to a cap for receiving an endoscopic device extending through the working channel of an endoscope.

BACKGROUND

Endoscopes are routinely used to provide a visual image of the internal anatomy of a patient while an endoscopic medical device is advanced through the working channel of the endoscope to a desired location within the anatomy. During use of the endoscope, a cap may be coupled to the proximal access port leading to the working channel of the endoscope. The cap, which may have an opening extending therethrough, may reduce the size of the opening of the working channel to accommodate the size of the endoscopic device. However, when an endoscopic device, such as a catheter, sphincterotome, basket, biopsy forceps, snare, or the like, is advanced alongside a guidewire through the opening of the cap, the guidewire distorts the opening such that a good seal around the endoscopic device cannot be maintained. Distortion of the opening of the cap may frustrate the seal around the endoscopic device such that fluids may egress through the opening of the cap past the endoscopic device.

Therefore, a need exists to provide an endoscope cap which may be coupled to the proximal access port of a working channel of an endoscope which may complement an endoscopic device and one or more guidewires while the endoscopic device is positioned in the opening of the cap and the one or more guidewires extend along the endoscopic device. The cap may substantially inhibit the egress of fluid from the working channel while the endoscopic device and one or more guidewires are positioned through the working channel by way of the cap.

SUMMARY

The disclosure is directed to a cap for inhibiting egress of fluid from an endoscope working channel.

Accordingly, one illustrative embodiment is a cap including an outer shell configured to be coupled to an access port of an endoscope, and a resilient member, at least a portion of which is positioned interior of the inner peripheral surface of the outer shell. The resilient member includes an upper surface, a lower surface, an outer peripheral surface and a central opening sized to accommodate an endoscopic instrument therethrough. The resilient member further includes a slit extending outward from the circumferential surface of the central opening toward the outer peripheral surface of the resilient member.

Another illustrative embodiment is a method of inhibiting egress of fluids from a working channel of an endoscope. A cap including a tubular shell and a resilient member having a central opening and a slit extending outward from the central opening may be coupled to a portion of an endoscope leading to a working channel. An endoscopic instrument may be advanced through the central opening of the resilient member of the cap into the working channel of the endoscope. A guidewire may be positioned in the slit of the resilient member at a location radially outward from the circumferential wall of the central opening. Thus, the central opening may conform around the endoscopic device and/or the slit may conform around the guidewire, thereby substantially preventing egress of fluid from the working channel of the endoscope.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
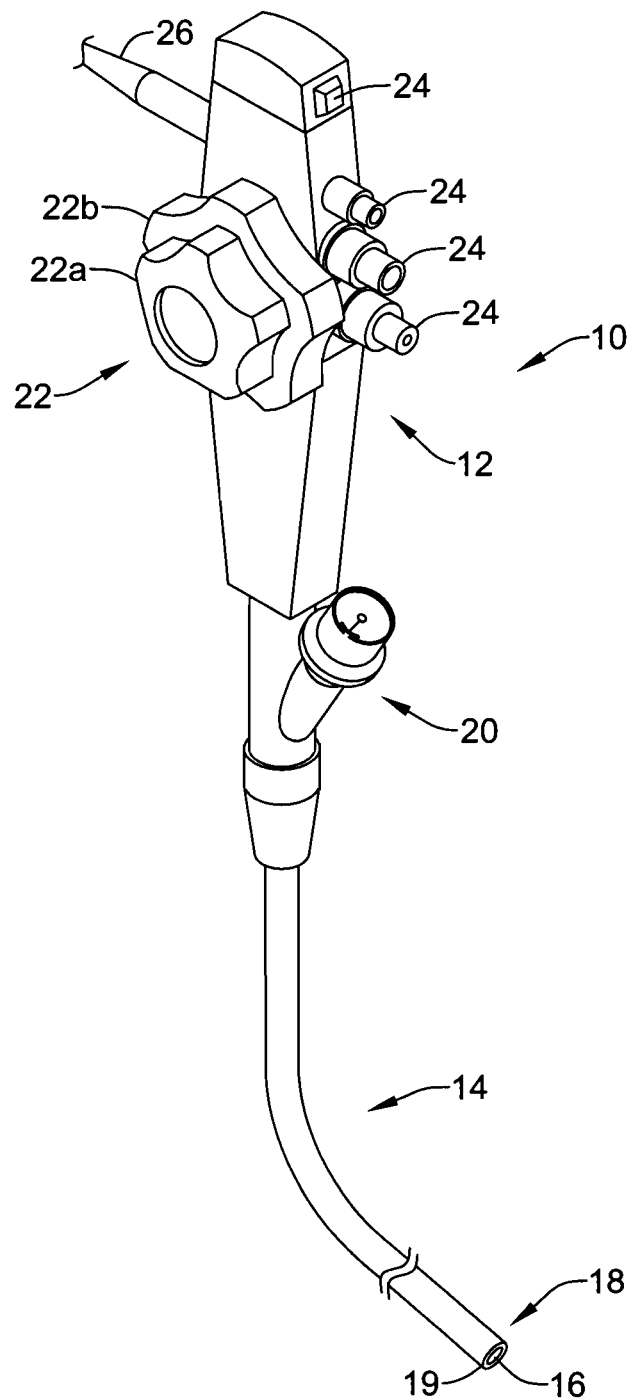
FIG. 1 is an illustrative embodiment of an exemplary endoscope.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used in this specification and the appended claims, the terms "upper" and "lower", when used to describe various disclosed components or features, are intended to describe the relative location of the specified components or features in relation to the access port of the endoscope. In other words, a component or feature modified by the term "lower" would suggest the component or feature is located in closer proximity to the access port than a similar component or feature modified by the term "upper".

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Now referring to the Figures, an exemplary endoscope is illustrated in FIG. 1. The endoscope 10 may be any of a number of types of endoscopes usually identified by the particular anatomy desired to be reached. For example, but not limitation, the endoscope 10 may be a bronchoscope, colonoscope, duodenoscope, esophagoscope, or other endoscope known in the art. The endoscope 10 may include a handpiece 12 and an elongate shaft 14 extending distally from the handpiece 12 to a distal tip 18. The elongate shaft 14 may include a lumen defining a working channel 16 extending through the elongate shaft 14 from a distal end 19 proximate the distal tip 18 of the elongate shaft 14 to an access port 20 in the handpiece 12 or other portion of the endoscope 10. Although an endoscope with a single working channel is illustrated in FIG. 1, it is noted that in other embodiments, the endoscope 10 may include multiple working channels, as desired.

The handpiece 12 may include one, or a plurality of controls 22, such as rotating knobs, which may be used to control movement of the distal end 18 of the elongate shaft 14 during operation. For example, a first rotating knob 22a may control up and down movement or deflection of the distal tip 18 of the elongate shaft 14, while a second rotating knob 22b may control side-to-side movement or deflection of the distal tip 18 of the elongate shaft 14.

The handpiece 12 may also include one, or a plurality of buttons 24, which may be used to activate suction or deliver fluid such as air, saline and/or water, etc. through a lumen of the endoscope 10 or perform other functions as desired. Additionally, the handpiece 12 may include an optical cable 26 connected to an external light source (not shown).

Figure 2:
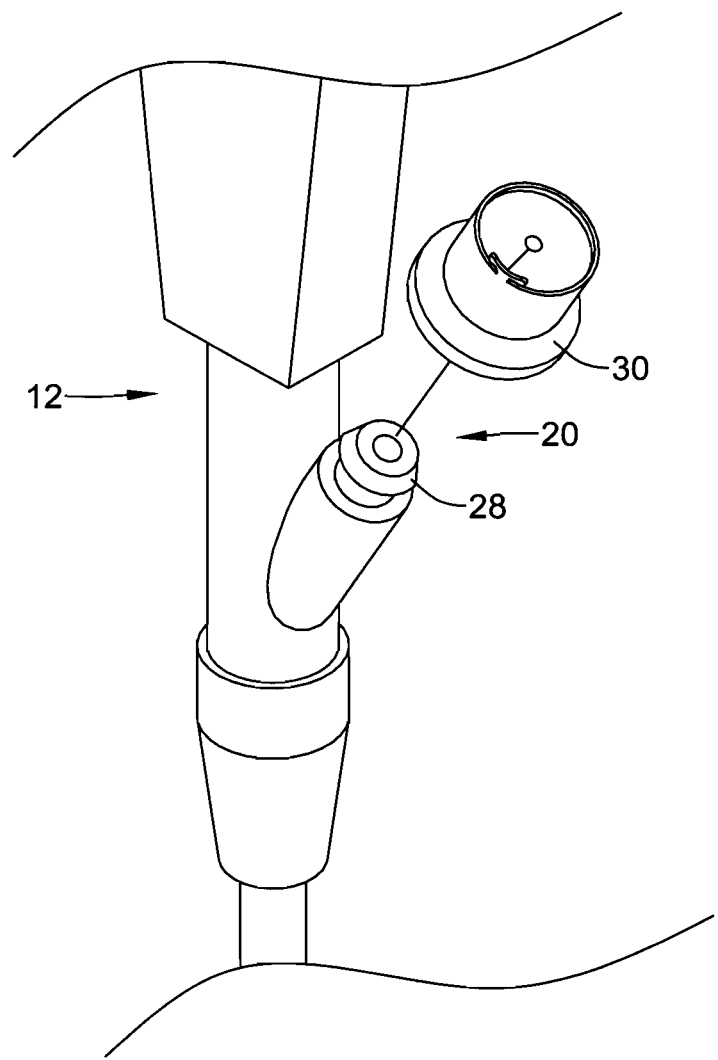
FIG. 2 is an expanded view of a portion of the exemplary endoscope of FIG. 1 including the access port leading to a working channel.

The access port 20 of the handpiece 12 providing access to the working channel 16 of the endoscope 10 may more readily be illustrated in FIG. 2. The access port 20, which may extend from the side of the endoscope 10 or at another location, may include a coupling portion 28 for coupling a cap 30 to the access port 20. The cap 30, which may be removably attached or permanently attached to the access port 20, may provide access for inserting and/or advancing an endoscopic device through the working channel 16 of the endoscope 10.

Figure 3:
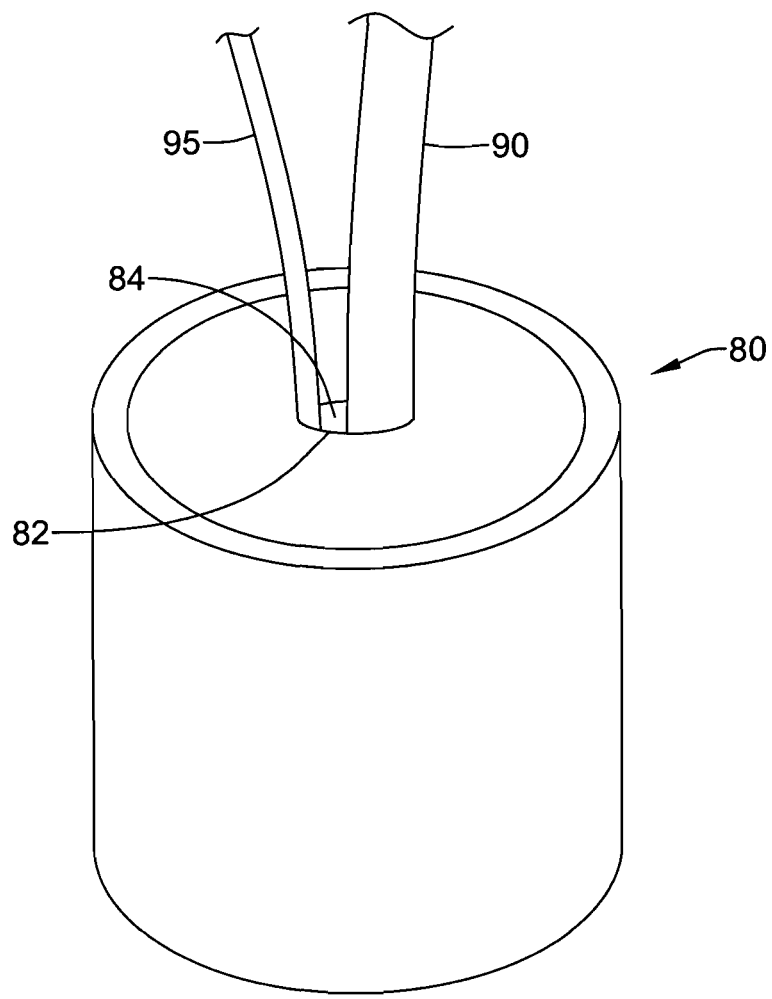
FIG. 3 is a depiction of an endoscope cap generally known in the art.

FIG. 3 illustrates a cap 80 such as those or illustrative of those known in the prior art which includes a central opening 82 extending therethrough. As shown in FIG. 3, when an endoscopic device 90 and a guidewire 95 are inserted through the cap 80, the central opening 82 is distorted from its circular shape such that a gap 84 is created. The gap 84 prevents the cap 80 from sufficiently sealing around the endoscopic device 90 because the presence of the guidewire 95 prohibits the surface of the central opening 82 from engaging the endoscopic device 90 in the region proximate the guidewire 95. The gap 84 which is unavoidably formed greatly increases the possibility of fluid egressing from the cap 80 by way of the gap 84.

Figure 4:
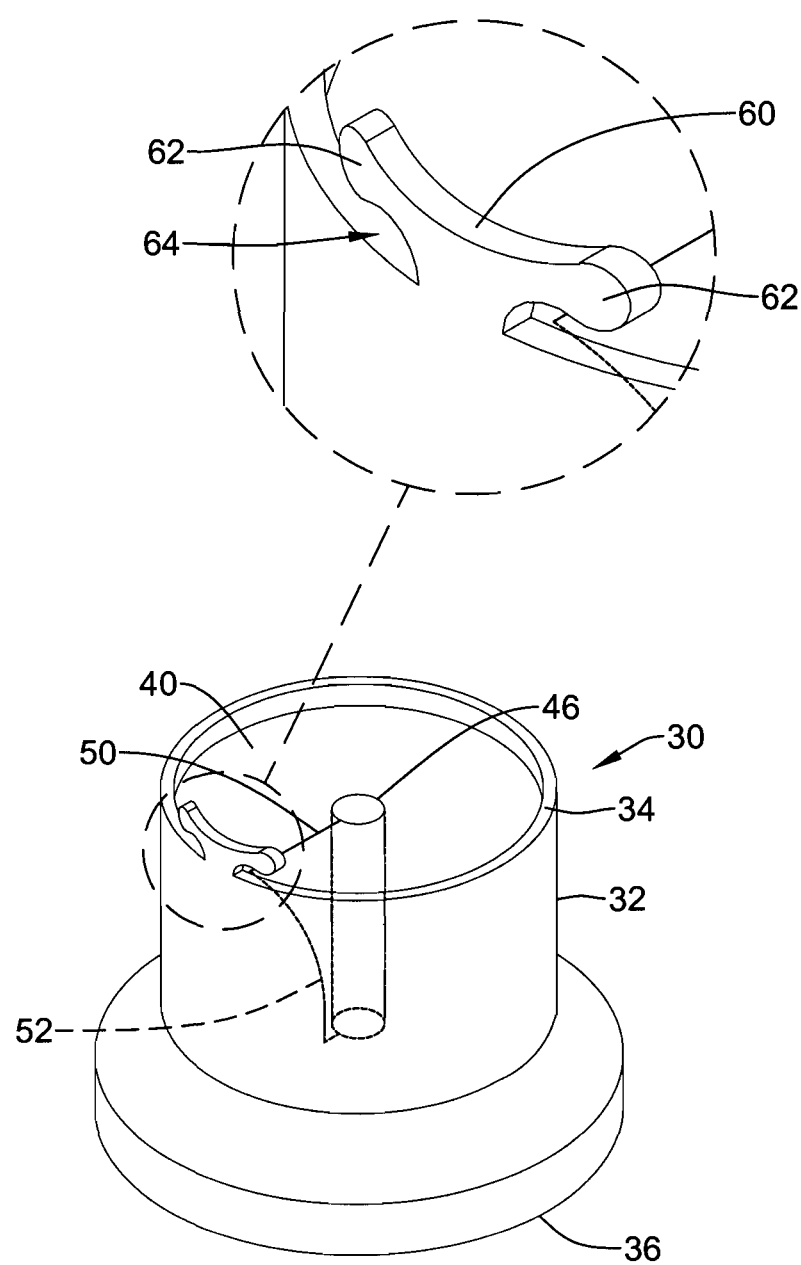
FIG. 4 is an illustrative embodiment of a cap for coupling to an access port of an endoscope.
Figure 4A:
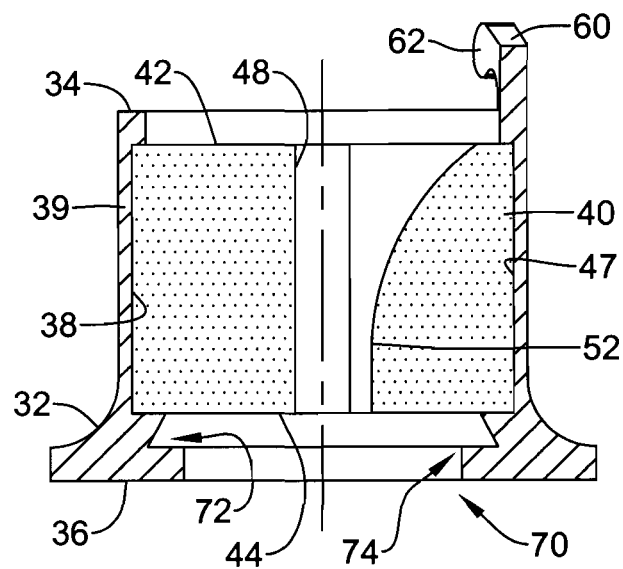
FIG. 4A is a cross-sectional view of the exemplary cap illustrated in FIG. 4.
Figure 4B:
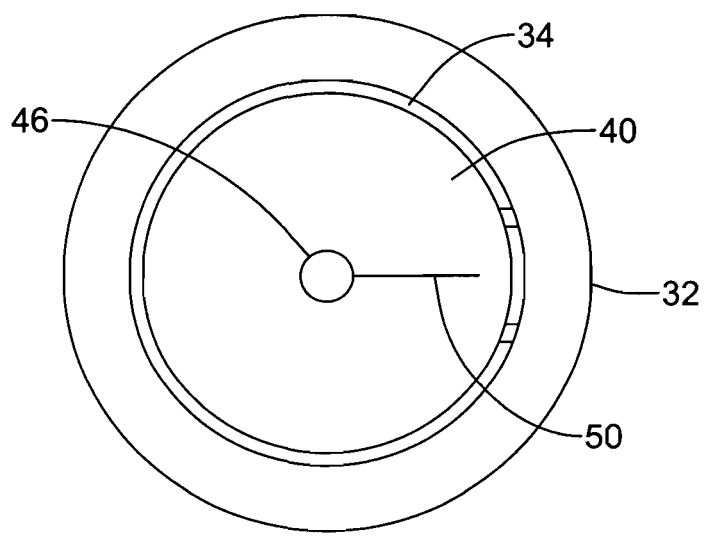
FIG. 4B is a top view of the exemplary cap illustrated in FIG. 4.

The cap 30 shown in FIG. 4, as well as FIGS. 4A and 4B, overcomes inadequacies of the prior art caps such as those shown in FIG. 3. The cap 30 may include a relatively rigid outer shell 32 having an upper end 34, a lower end 36 and an inner peripheral surface 38 extending between the upper end 34 and the lower end 36. In some embodiments, the shell 32 may be a generally tubular member having an annular wall 39.

As shown in FIG. 4A, the cap 30 may include a coupling portion 70 which may mate with, engage with, or otherwise include geometry which may complement the geometry of the coupling portion 28 of the access port 20. Thus, the cap 30 may be removably attached to, or permanently attached to the access port 20 of the endoscope 10. In describing the cap 30 as being removably attached to the access port 20, the intention is to describe the relationship of the cap 30 and the access port 20 as being separable from one another under ordinary operating conditions without damaging and/or causing unintended consequences of the components. Furthermore, in describing the cap 30 as being permanently attached to the access port 20, the intention is to describe the relationship of the cap 30 and the access port 20 as not being separable from one another under ordinary operating conditions without damaging and/or causing unintended consequences of the components. For instance, in some embodiments the endoscope 10 and the cap 30 may be formed of a unitary or monolithic construction. In such embodiments, the collective endoscope 10 and cap 30 may be intended for single use and then discarded, or the collective endoscope 10 and cap 30 may be sterilized prior to a subsequent use.

As illustrated in FIG. 4A, the coupling portion 70 of the cap 30 may include a groove 72, such as an annular groove, and/or a lip 74, such as an annular lip, defined in the inner peripheral surface 38 of the cap 30. The groove 72 and/or the lip 74 may be configured to interlock with or otherwise engage with a complementary geometry of the coupling portion 28 of the access port 20. However, in other embodiments, the coupling portion 70 may include another geometry configured to interlock with or otherwise engage with a complementary geometry of the coupling portion 28 of the access port 20. For example, the coupling portion 70 may include a threaded portion, such as a female threaded portion, which may mate with a threaded portion, such as a male threaded portion, of the coupling portion 28 of the access port 20. In yet other embodiments, the cap 30 may be adhesively bonded or heat bonded to the access port 20, for example. In some embodiments, the coupling portion 70 may be a compliant portion of the cap 30 which may radially expand to snap over, frictionally engage, or otherwise mate with the geometry of the access port 20.

In some embodiments, such as the embodiment of FIG. 4, the cap 30 may additionally include a guidewire locking structure 60. In some embodiments, the guidewire locking structure 60 may be a unitary portion of the shell 32, whereas in other embodiments, the guidewire locking structure 60 may be a separate component coupled to, secured to, or otherwise brought into association with the cap 30. The guidewire locking structure 60 may be configured to selectively secure a guidewire to the cap 30 for use during a medical procedure. In operation, a desired position of a guidewire may be maintained relative to the endoscope 10 by securing the guidewire with the guidewire locking structure 60.

The guidewire locking structure 60 may include any of a variety of configurations. For example, the guidewire locking structure 60 may include one or more ears or tabs 62 forming an opening 64 for receiving a guidewire. As shown in FIG. 4, the guidewire locking structure 60 may include two ears 62 opposing one another and extending in opposite directions. Each of the ears 62 may extend above the upper end 34 of the shell 32, forming an opening 64 sized to accommodate a guidewire between the ear 62 and the upper end 34 of the shell 32. Thus, multiple guidewires may be selectively secured to the cap 30 with such a configuration. In other embodiments, the guidewire locking structure 60 may include one or more slots, notches, grooves or other configuration for receiving a guidewire.

A resilient member 40 may be at least in part positioned interior of the inner peripheral surface 38 of the shell 32. In some embodiments, the resilient member 40 may be formed of a polymeric material, a foam material, or similar material providing the resilient member 40 with a degree of resiliency and/or conformability.

The resilient member 40 may be formed of any suitable material. Some suitable materials include polymeric and/or synthetic foams, rubber, silicone and/or elastomers, including thermoplastic polymers such as polyurethane.

In some embodiments, such as the embodiment of FIG. 4, the resilient member 40 may be a generally cylindrical member having an outer circumferential surface. In some embodiments, the outer peripheral surface 47 of the resilient member 40 may be bonded to, adhered to, secured to, engaged with, or otherwise in contact with the inner peripheral surface 38 of the shell 32. The resilient member 40 may include an upper surface 42, a lower surface 44 (shown in FIG. 4A) and a central opening 46 having a circumferential surface 48 extending along the central longitudinal axis of the cap 30 between the upper surface 42 and the lower surface 44 of the resilient member 40. In some embodiments, the central opening 46 may be cylindrical, conical, frusta-conical, or portions may be cylindrical, conical and/or frusta-conical. In some embodiments, such as the embodiment illustrated in FIG. 4A, the upper surface 42 may be recessed into the shell 32 such that the upper surface 42 of the resilient member 40 is nonplanar with the upper end 34 of the shell 32. In some embodiments, the upper surface 42 of the resilient member 40 may extend up to or beyond the upper end 34 of the shell 32. For instance, in other embodiments, the upper surface 42 of the resilient member 40 may be raised from, flush with, or planar with, the upper end 34 of the shell 32. In yet other embodiments, the upper surface 42 of the resilient member 40, which may be convex or concave, may be located below, extend up to or extend beyond the upper end 34 of the shell 32. In some embodiments, the upper surface 42 of the resilient member 40 may be raised from, flush with, or planar with the upper end 34 of the shell 32.

The resilient member 40 may have a length measured in the direction of the central longitudinal axis of the cap 30, and the shell 32, likewise, may have a length measured in the direction of the central longitudinal axis of the cap 30. In some embodiments, the resilient member 40 may extend a majority of, or a substantial portion of the length of the shell 32. In some embodiments, the length of the shell 32 may be in the range of about 2 to about 4 centimeters, whereas the length of the resilient member 40 may be in the range of about 1 to about 3 centimeters. In one embodiment, the length of the shell 32 may be about 3 centimeters, whereas the length of the resilient member 40 may be about 2.6 centimeters. In some embodiments, the length of the resilient member 40 may be 50% or more, 60% or more, 75% or more, or 85% or more of the length of the shell 32. Although some suitable dimensions are disclosed, one of skill in the art, incited by the present disclosure, would understand that desired dimensions may deviate from those expressly disclosed.

The resilient member 40 may also include one or more, or a plurality of slits 50 extending from the circumferential surface 48 of the central opening 46 generally toward the outer peripheral surface 47 of the resilient member 40. One slit 50 is illustrated in FIG. 4. However, in other embodiments, the resilient member 40 may include two, three, four, five, or more slits. The one or more, or plurality of slits 50 may be adapted to receive a guidewire extending therethrough during a medical procedure, as described later herein.

The slit(s) 50 may extend outward from the circumferential surface 48 of the central opening 46, or the slit(s) 50 may extend outward over another path. For example, the slit(s) 50 may extend radially outward from the circumferential surface 48 to the outer edge 52 of the slit(s) 50. In some embodiments, the slit(s) 50 may extend outward in a linear pathway, or the slit(s) 50 may extend outward in a curvilinear fashion. As shown in FIG. 4A, the slit(s) 50 may extend from the upper surface 42 to the lower surface 44 of the resilient member 40. In some embodiments, the slit(s) 50 may extend further outward from the central longitudinal axis at a location proximate the upper surface 42 of the resilient member 40 than at a location proximate the lower surface 44 of the resilient member 40. For example, the slit(s) 50 may extend in a curvilinear fashion or a linear fashion from a location radially outward from the central longitudinal axis proximate the lower surface 44 toward a location radially outward from the central longitudinal axis proximate the upper surface 42. In other words, the outer edge 52 of the slit(s) 50 may be curvilinear or linear, for example. In some embodiments, the outer edge 52 of the slit(s) 50 may be oblique or nonparallel with the central longitudinal axis of the cap 30. However, in other embodiments, the outer edge 52 of the slit(s) 50 may be parallel with the central longitudinal axis of the cap 30.

Figure 5:
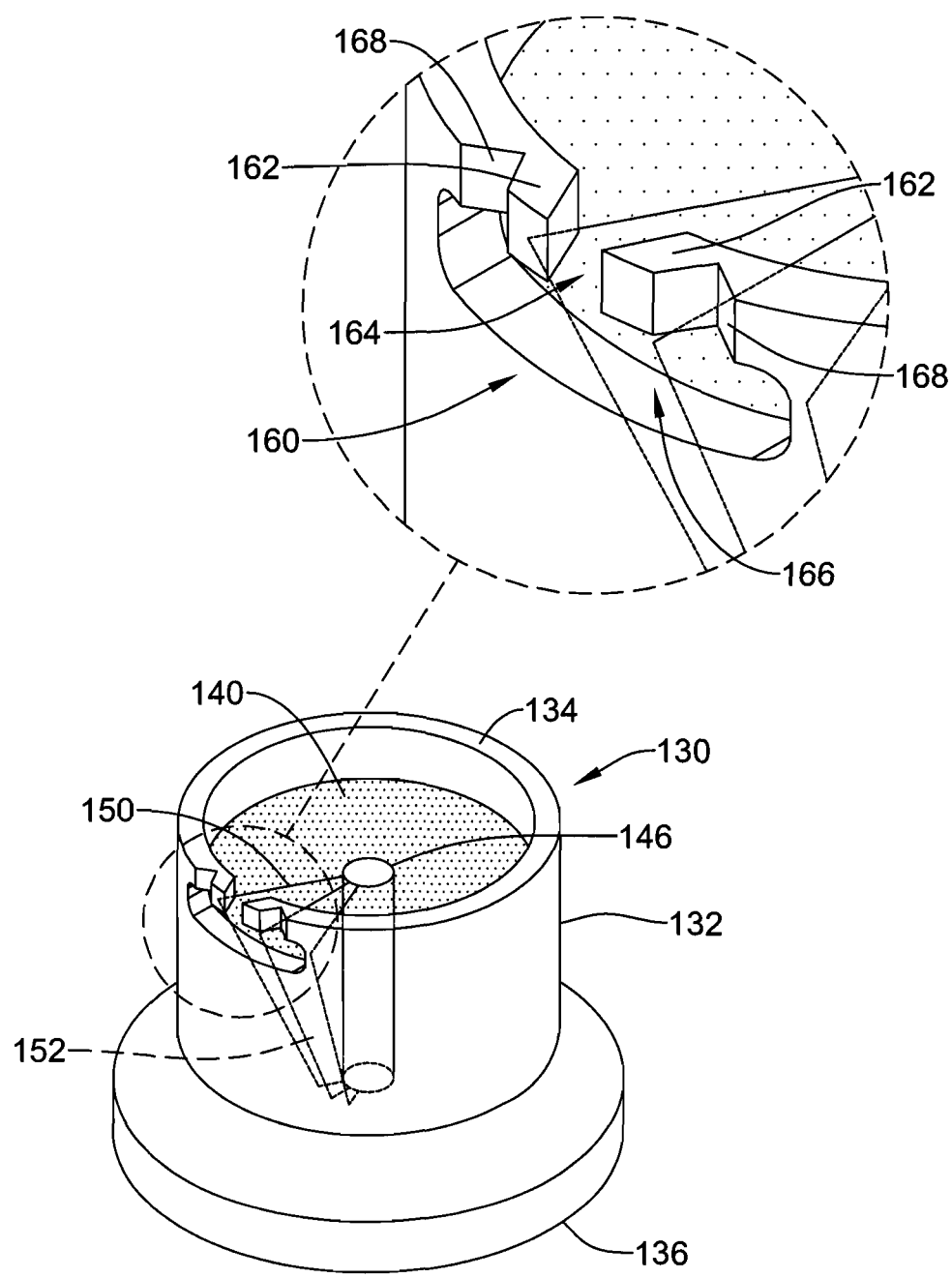
FIG. 5 is another illustrative embodiment of a cap for coupling to an access port of an endoscope.
Figure 5A:
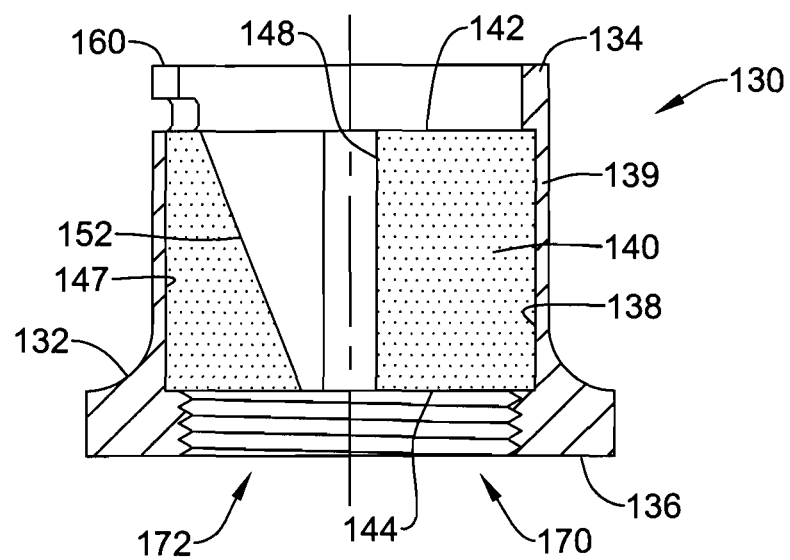
FIG. 5A is a cross-sectional view of the exemplary cap illustrated in FIG. 5.
Figure 5B:
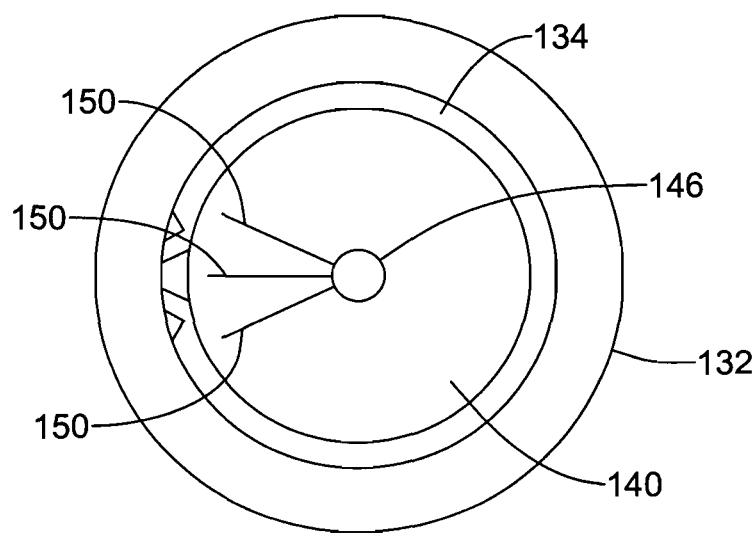
FIG. 5B is a top view of the exemplary cap illustrated in FIG. 5.

Another exemplary cap 130 is shown in FIG. 5, as well as FIGS. 5A and 5B. The cap 130 may include a relatively rigid outer shell 132 having an upper end 134, a lower end 136 and an inner peripheral surface 138 extending between the upper end 134 and the lower end 136. In some embodiments, the shell 132 may be a generally tubular member having an annular wall 139.

As shown in FIG. 5A, the cap 130 may include a coupling portion 170 which may mate with, engage with, or otherwise include geometry which may complement the geometry of the coupling portion 28 of the access port 20. Thus, the cap 130 may be removably attached to, or permanently attached to the access port 20 of the endoscope 10. In describing the cap 130 as being removably attached to the access port 20, the intention is to describe the relationship of the cap 130 and the access port 20 as being separable from one another under ordinary operating conditions without damaging and/or causing unintended consequences of the components. Furthermore, in describing the cap 130 as being permanently attached to the access port 20, the intention is to describe the relationship of the cap 130 and the access port 20 as not being separable from one another under ordinary operating conditions without damaging and/or causing unintended consequences of the components. For instance, in some embodiments the endoscope 10 and the cap 130 may be formed of a unitary or monolithic construction. In such embodiments, the collective endoscope 10 and cap 130 may be intended for single use and then discarded, or the collective endoscope 10 and cap 130 may be sterilized prior to a subsequent use.

As illustrated in FIG. 5A, the coupling portion 170 of the cap 130 may include a threaded portion 172, such as a female threaded portion. The threaded portion 172 may be configured to threadedly engage a complementary threaded portion, such as a male threaded portion, of the coupling portion 28 of the access port 20. However, in other embodiments the coupling portion 170 may include other geometry configured to interlock with or otherwise engage with a complementary geometry of the coupling portion 28 of the access port 20. For example, the coupling portion 170 may include one or more grooves, such as annular grooves, and/or one or more lips, such as annular lips, which may mate with the coupling portion 28 of the access port 20. In yet other embodiments, the cap 130 may be adhesively bonded or heat bonded to the access port 20, for example. In some embodiments, the coupling portion 170 may be a compliant portion of the cap 130 which may radially expand to snap over, frictionally engage, or otherwise mate with the geometry of the access port 20.

In some embodiments, such as the embodiment of FIG. 5, the cap 130 may additionally include a guidewire locking structure 160. In some embodiments, the guidewire locking structure 160 may be a unitary portion of the shell 132, whereas in other embodiments, the guidewire locking structure 160 may be a separate component coupled to, secured to, or otherwise brought into association with the cap 130. The guidewire locking structure 160 may be configured to selectively secure a guidewire to the cap 130 for use during a medical procedure. In operation, a desired position of a guidewire may be maintained relative to the endoscope 10 by securing the guidewire with the guidewire locking structure 160.

The guidewire locking structure 160 may include any of a variety of configurations. For example, the guidewire locking structure 160 may include an opening 164 extending through the annular wall 139 of the shell 132, forming one or more ears 162. As shown in FIG. 5, the guidewire locking structure 160 may include two ears 162 opposing one another with a slot 166 formed between the pair of ears 162. Each of the ears 162 may include a notch or recess 168, or other structure for retaining a guidewire. Therefore, a guidewire may be directed outward through the slot 166 and secured behind one of the ears 162. Thus, multiple guidewires may be selectively secured to the cap 130 with such a configuration. In other embodiments, the guidewire locking structure 160 may include one or more slots, notches, grooves or other configuration for receiving a guidewire.

A resilient member 140 may be positioned interior of the inner peripheral surface 138 of the shell 132. In some embodiments, the resilient member 140 may be formed of a polymeric material, a foam material, or similar material providing the resilient member 140 a degree of resiliency and/or conformability.

The resilient member 140 may be formed of any suitable material. Some suitable materials include polymeric and/or synthetic foams, rubber, silicone and/or elastomers, including thermoelastic polymers such as polyurethane.

In some embodiments, such as the embodiment of FIG. 5, the resilient member 140 may be a generally cylindrical member having an outer circumferential surface. In some embodiments, the outer peripheral surface 147 of the resilient member 140 may be bonded to, adhered to, secured to, engaged with, or otherwise in contact with the inner peripheral surface 138 of the shell 132. The resilient member 140 may include an upper surface 142, a lower surface 144 (shown in FIG. 5A) and a central opening 146 having a circumferential surface 148 extending along the central longitudinal axis of the cap 130 between the upper surface 142 and the lower surface 144 of the resilient member 140. In some embodiments, the central opening 146 may be cylindrical, conical, frusta-conical, or portions may be cylindrical, conical and/or frusta-conical. In some embodiments, such as the embodiment illustrated in FIG. 5A, the upper surface 142 may be recessed into the shell 132 such that the upper surface 142 of the resilient member 140 is nonplanar with the upper end 134 of the shell 132. In some embodiments, the upper surface 142 of the resilient member 140 may extend up to or extend beyond the upper end 134 of the shell 132. In yet other embodiments, the upper surface 142 of the resilient member 140, which may be convex or concave, may be located below, extend up to or beyond the upper end 134 of the shell 132. In some embodiments, the upper surface 142 of the resilient member 140 may be raised from, flush with, or planar with the upper end 134 of the shell 132.

The resilient member 140 may have a length measured in the direction of the central longitudinal axis of the cap 130, and the shell 132, likewise, may have a length measured in the direction of the central longitudinal axis of the cap 130. In some embodiments, the resilient member 140 may extend a majority, or substantial portion of the length of the shell 132. In some embodiments, the length of the shell 132 may be in the range of about 2 to about 4 centimeters, whereas the length of the resilient member 140 may be in the range of about 1 to about 3 centimeters. In one embodiment, the length of the shell 132 may be about 3 centimeters, whereas the length of the resilient member 140 may be about 2.6 centimeters. In some embodiments, the length of the resilient member 140 may be 50% or more, 60% or more, 75% or more, or 85% or more of the length of the shell 132. Although some suitable dimensions are disclosed, one of skill in the art, incited by the present disclosure, would understand that desired dimensions may deviate from those expressly disclosed.

The resilient member 140 may also include one or more, or a plurality of slits 150 extending from the circumferential surface 148 of the central opening 146 toward the outer peripheral surface 147 of the resilient member 140. Three slits 150 are illustrated in FIG. 5. However, in other embodiments the resilient member 140 may include one, two, four, five, or more slits. The one or more, or plurality of slits 150 may be adapted to receive a guidewire extending therethrough during a medical procedure, as described later herein.

The slits 150 may extend outward from the circumferential surface 148 of the central opening 146, or the slits 150 may extend outward over another path. For example, the slits 150 may extend radially outward from the circumferential surface 148 to the outer edge 152 of the slits 150. In some embodiments, the slits 150 may extend outward in a linear pathway, or the slits 150 may extend outward in a curvilinear fashion. As shown in FIG. 5A, the slits 150 may extend from the upper surface 142 to the lower surface 144 of the resilient member 140. In some embodiments, the slits 150 may extend further outward from the central longitudinal axis at a location proximate the upper surface 142 of the resilient member 140 than at a location proximate the lower surface 144 of the resilient member 140. For example, the slits 150 may extend in a curvilinear fashion or a linear fashion from a location radially outward from the central longitudinal axis proximate the lower surface 144 toward a location radially outward from the central longitudinal axis proximate the upper surface 142. In other words, the outer edge 152 of the slits 150 may be curvilinear or linear, for example. In some embodiments, the outer edge 152 of the slits 150 may be oblique or nonparallel with the central longitudinal axis of the cap 130. However, in other embodiments, the outer edge 152 of the slits 150 may be parallel with the central longitudinal axis of the cap 130.

In some embodiments, the slits 150 may be radially arranged such that a first slit is located less than 90 degrees from an adjacent slit. In some embodiments, a first slit may be located about 5 to about 30 degrees from an adjacent slit, or in some embodiments, a first slit may be located about 10 to about 15 degrees from an adjacent slit. However, in other embodiments the slits 150 may be arranged in a different configuration as desired.

Figure 6:
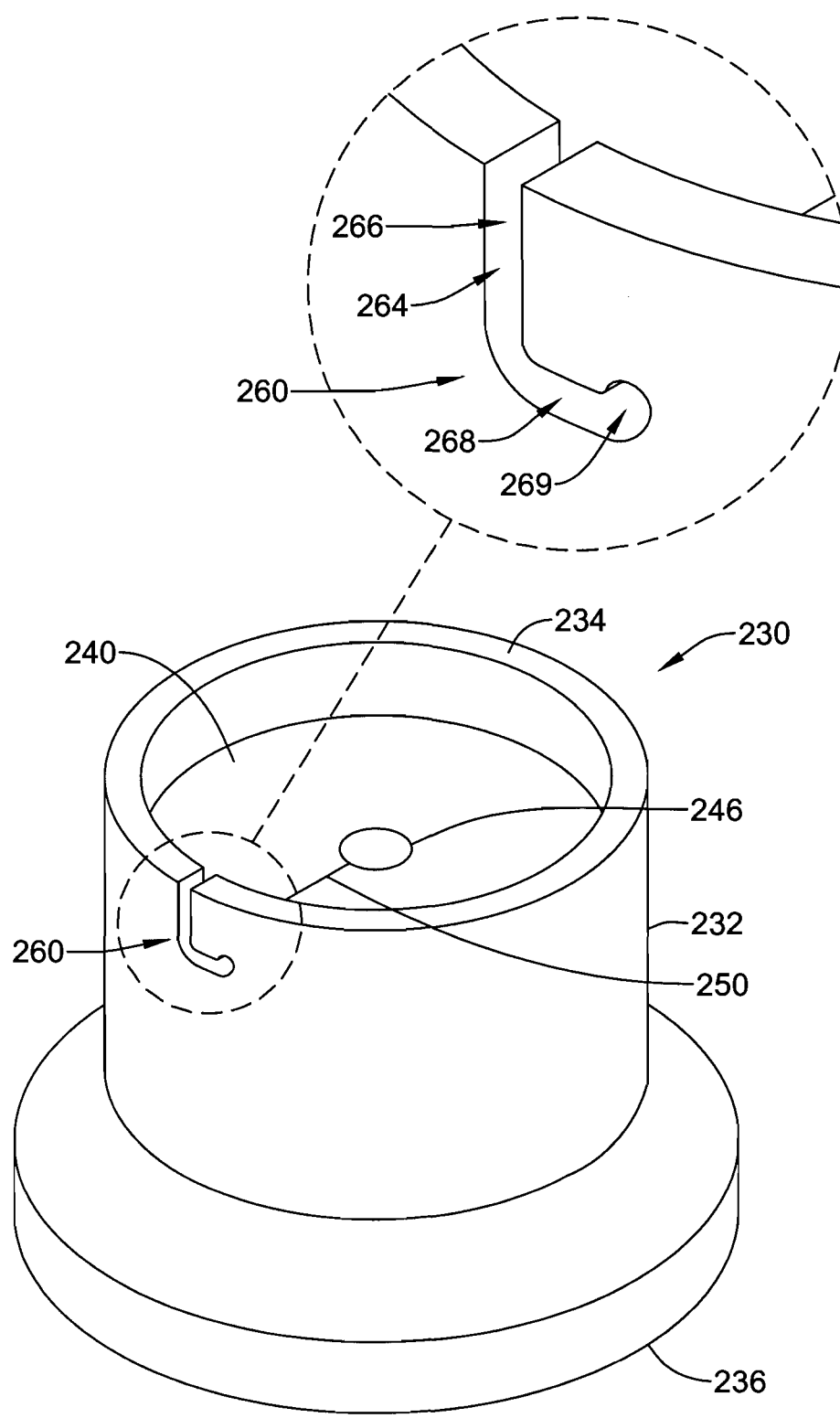
FIG. 6 is another illustrative embodiment of a cap for coupling to an access port of an endoscope.
Figure 6A:
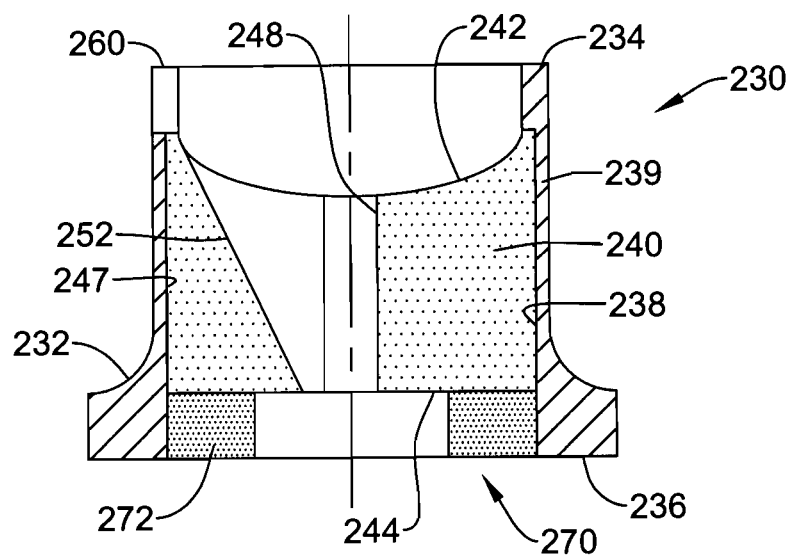
FIG. 6A is a cross-sectional view of the exemplary cap illustrated in FIG. 6.
Figure 6B:
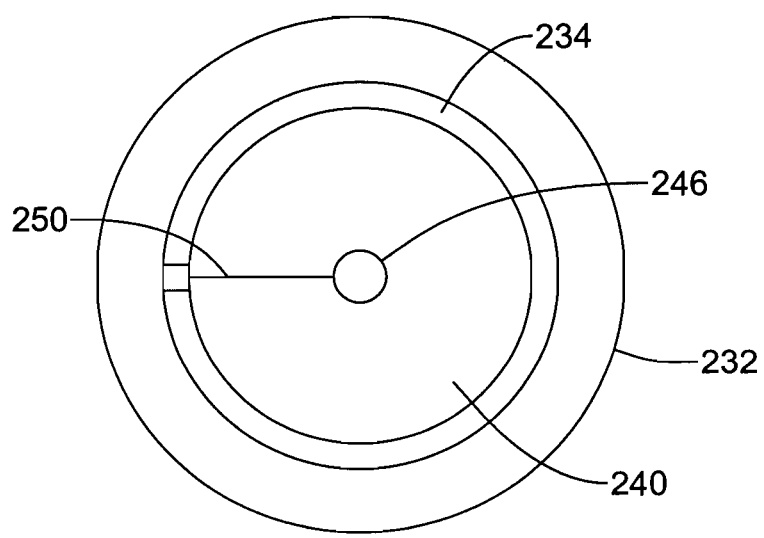
FIG. 6B is a top view of the exemplary cap illustrated in FIG. 6.

Another exemplary cap 230 is shown in FIG. 6, as well as FIGS. 6A and 6B. The cap 230 may include a relatively rigid outer shell 232 having an upper end 234, a lower end 236 and an inner peripheral surface 238 extending between the upper end 234 and the lower end 236. In some embodiments, the shell 232 may be a generally tubular member having an annular wall 239.

As shown in FIG. 6A, the cap 230 may include a coupling portion 270 which may engage with the coupling portion 28 of the access port 20. Thus, the cap 230 may be removably attached to, or permanently attached to the access port 20 of the endoscope 10. In describing the cap 230 as being removably attached to the access port 20, the intention is to describe the relationship of the cap 230 and the access port 20 as being separable from one another under ordinary operating conditions without damaging and/or causing unintended consequences of the components. Furthermore, in describing the cap 230 as being permanently attached to the access port 20, the intention is to describe the relationship of the cap 230 and the access port 20 as not being separable from one another under ordinary operating conditions without damaging and/or causing unintended consequences of the components. For instance, in some embodiments the endoscope 10 and the cap 230 may be formed of a unitary or monolithic construction. In such embodiments, the collective endoscope 10 and cap 230 may be intended for single use and then discarded, or the collective endoscope 10 and cap 230 may be sterilized prior to a subsequent use.

As illustrated in FIG. 6A, the coupling portion 270 of the cap 230 may include a compliant member 272 positioned within the outer shell 232 of the cap 230. The compliant member 272 may be formed of a resilient material such that the compliant member 272 may deform or yield when urged into contact with the access port 20. Thus, the compliant member 272, when at least slightly compressed, may snap over, frictionally engage, or otherwise mate with the geometry of the access port 20. In other embodiments, the outer shell 232 may be formed of a suitable compliant material which may deform or yield when urged into contact with the access port 20. In other embodiments, the coupling portion 270 may include another means for coupling the cap 230 to the access port 20 as described herein.

In some embodiments, such as the embodiment of FIG. 6, the cap 230 may additionally include a guidewire locking structure 260. In some embodiments, the guidewire locking structure 260 may be a unitary portion of the shell 232, whereas in other embodiments, the guidewire locking structure 260 may be a separate component coupled to, secured to, or otherwise brought into association with the cap 230. The guidewire locking structure 260 may be configured to selectively secure a guidewire to the cap 230 for use during a medical procedure. In operation, a desired position of a guidewire may be maintained relative to the endoscope 10 by securing the guidewire with the guidewire locking structure 260.

The guidewire locking structure 260 may include any of a variety of configurations. For example, the guidewire locking structure 260 may include a slot 264 extending through the annular sidewall 239 of the shell 232. As shown in FIG. 6, the slot 264 may be an "L" shape or other shape as desired. The "L" shaped slot 264 includes a first portion 266 extending in a first direction and a second portion 268 extending from the first portion 266 in a second direction. In the embodiment shown, the first portion 266 is perpendicular to the second portion 268. However, in other embodiments the first portion 266 may be oblique to the second portion 268. The second portion 268 of the slot 264 may include a detent 269 for retaining a guidewire. Thus, a guidewire may be retained by the guidewire locking structure 260 by directing the guidewire outward through the slot 264. The guidewire may be advanced downward through the first portion 266 toward the second portion 266 and then across the second portion 268 to the detent 269 such that the guidewire may be secured in the detent 269. It is to be noted that in some embodiments the detent 269 need not be present in order to retain the guidewire in the slot 264. In other embodiments, the guidewire locking structure 260 may include other means for receiving and/or retaining a guidewire during a medical procedure.

A resilient member 240 may be positioned interior of the inner peripheral surface 238 of the shell 232. In some embodiments, the resilient member 240 may be formed of a polymeric material, a foam material, or similar material providing the resilient member 240 a degree of resiliency and/or conformability.

The resilient member 240 may be formed of any suitable material. Some suitable materials include polymeric and/or synthetic foams, rubber, silicone and/or elastomers, including thermoelastic polymers such as polyurethane.

In some embodiments, such as the embodiment of FIG. 6, the resilient member 240 may be a generally cylindrical member having an outer circumferential surface. In some embodiments, the outer peripheral surface 247 of the resilient member 240 may be bonded to, adhered to, secured to, engaged with, or otherwise in contact with the inner peripheral surface 238 of the shell 232. The resilient member 240 may include an upper surface 242, a lower surface 244 (shown in FIG. 6A) and a central opening 246 having a circumferential surface 248 extending along the central longitudinal axis of the cap 230 between the upper surface 242 and the lower surface 244 of the resilient member 240. As shown in FIG. 6A, the upper surface 242 may be a concave surface. However, in other embodiments, the upper surface 242 may be a planar surface, a convex surface, or other configuration.

In some embodiments, the central opening 246 may be cylindrical, conical and/or frusta-conical, or portions may be cylindrical, conical and/or frusta-conical. In some embodiments, such as the embodiment illustrated in FIG. 6A, the upper surface 242 may be recessed into the shell 232 below the upper end 234 of the shell 232. In some embodiments, the upper surface 242 of the resilient member 240 may extend up to or extend beyond the upper end 234 of the shell 232.

The resilient member 240 may have a length measured in the direction of the central longitudinal axis of the cap 230, and the shell 232, likewise, may have a length measured in the direction of the central longitudinal axis of the cap 230. In some embodiments, the resilient member 240 may extend a majority, or substantial portion, of the length of the shell 232. In some embodiments, the length of the shell 232 may be in the range of about 2 to about 4 centimeters, whereas the length of the resilient member 240 may be in the range of about 1 to about 3 centimeters. In one embodiment, the length of the shell 232 may be about 3 centimeters, whereas the length of the resilient member 240 may be about 2.6 centimeters. In some embodiments, the length of the resilient member 240 may be 50% or more, 60% or more, 75% or more, or 85% or more of the length of the shell 232. Although some suitable dimensions are disclosed, one of skill in the art, incited by the present disclosure, would understand that desired dimensions may deviate from those expressly disclosed.

The resilient member 240 may also include one or more, or a plurality of slits 250 extending from the circumferential surface 248 of the central opening 246 toward the outer peripheral surface 247 of the resilient member 240. One slit 250 is illustrated in FIG. 6. However, in other embodiments, the resilient member 240 may include two, three, four, five, or more slits. The one or more, or plurality of slits 250 may be adapted to receive a guidewire extending therethrough during a medical procedure, as described later herein.

The slit(s) 250 may extend outward from the circumferential surface 248 of the central opening 246, or the slit(s) 250 may extend outward over another path. For example, the slit(s) 250 may extend radially outward from the circumferential surface 248 to the outer edge 252 of the slit(s) 250. In some embodiments, the slit(s) 250 may extend outward in a linear pathway, or the slit(s) 250 may extend outward in a curvilinear fashion. As shown in FIG. 6A, the slit(s) 250 may extend from the upper surface 242 to the lower surface 244 of the resilient member 240. In some embodiments, the slit(s) 250 may extend further outward from the central longitudinal axis at a location proximate the upper surface 242 of the resilient member 240 than at a location proximate the lower surface 244 of the resilient member 240. For example, the slit(s) 250 may extend in a curvilinear fashion or a linear fashion from a location radially outward from the central longitudinal axis proximate the lower surface 244 toward a location radially outward from the central longitudinal axis proximate the upper surface 242. In other words, the outer edge 252 of the slit(s) 250 may be curvilinear or linear, for example. As shown in FIG. 6A, at a location proximate the upper surface 242, the slit(s) 250 may extend outward to the inner surface 238 of the shell 232. In some embodiments, the outer edge 252 of the slit(s) 250 may be oblique or nonparallel with the central longitudinal axis of the cap 230. However, in other embodiments, the outer edge 252 of the slit(s) 250 may be parallel with the central longitudinal axis of the cap 230.

Figure 7:
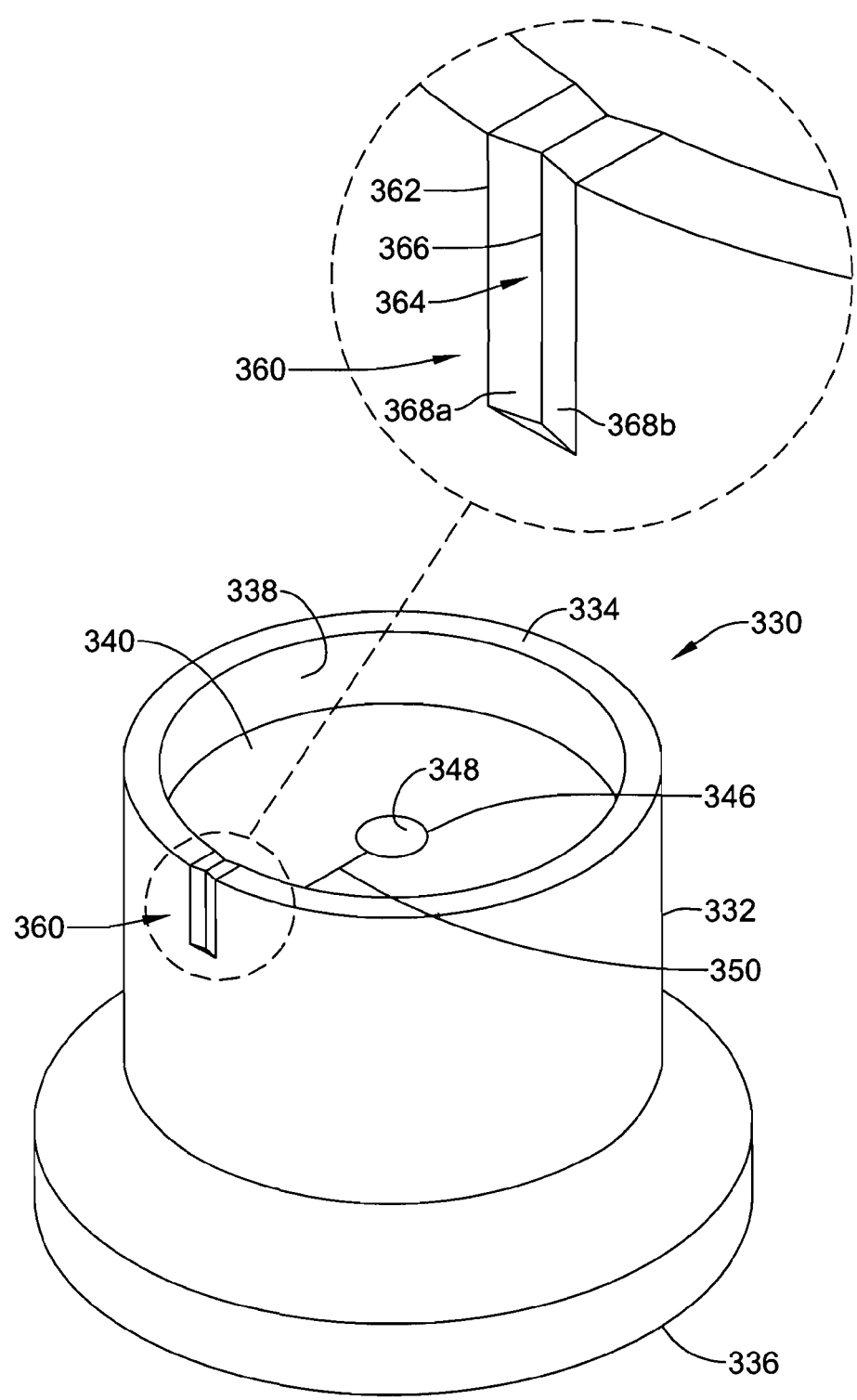
FIG. 7 is another illustrative embodiment of a cap for coupling to an access port of an endoscope.

Another exemplary embodiment of a cap 330 is shown in FIG. 7. The cap 330 may include a relatively rigid outer shell 332 having an upper end 334, a lower end 336 and an inner peripheral surface 338 extending between the upper end 334 and the lower end 336. In some embodiments, the shell 332 may be a generally tubular member having an annular wall.

A resilient member 340 may be positioned interior of the inner peripheral surface 338 of the shell 332. In some embodiments, the resilient member 340 may be formed of a polymeric material, a foam material, or similar material providing the resilient member 340 a degree of resiliency and/or conformability.

The resilient member 340 may be formed of any suitable material. Some suitable materials include polymeric and/or synthetic foams, rubber, silicone and/or elastomers, including thermoelastic polymers such as polyurethane.

In some embodiments, such as the embodiment of FIG. 7, the resilient member 340 may be a generally cylindrical member having an outer circumferential surface. In some embodiments, the outer peripheral surface of the resilient member 340 may be bonded to, adhered to, secured to, engaged with, or otherwise in contact with the inner peripheral surface 338 of the shell 332. The resilient member 340 may include central opening 346 having a circumferential surface 348 extending along the central longitudinal axis of the cap 330 between the upper surface and the lower surface of the resilient member 340.

In some embodiments, the central opening 346 may be cylindrical, conical and/or frusta-conical, or portions may be cylindrical, conical and/or frusta-conical. In some embodiments, such as the embodiment illustrated in FIG. 7, the upper surface of the resilient member 340 may be recessed into the shell 332 below the upper end 334 of the shell 332. However, in some embodiments, the upper surface of the resilient member 340 may extend up to or beyond the upper end 334 of the shell 332.

The resilient member 340 may have a length measured in the direction of the central longitudinal axis of the cap 330, and the shell 332, likewise, may have a length measured in the direction of the central longitudinal axis of the cap 330. In some embodiments, the resilient member 340 may extend a majority, or substantial portion, of the length of the shell 332. In some embodiments, the length of the shell 332 may be in the range of about 2 to about 4 centimeters, whereas the length of the resilient member 340 may be in the range of about 1 to about 3 centimeters. In one embodiment, the length of the shell 332 may be about 3 centimeters, whereas the length of the resilient member 340 may be about 2.6 centimeters. In some embodiments, the length of the resilient member 340 may be 50% or more, 60% or more, 75% or more, or 85% or more of the length of the shell 332. Although some suitable dimensions are disclosed, one of skill in the art, incited by the present disclosure, would understand that desired dimensions may deviate from those expressly disclosed.

The resilient member 340 may also include one or more, or a plurality of slits 350 extending from the circumferential surface 348 of the central opening 346 toward the outer peripheral surface of the resilient member 340. One slit 350 is illustrated in FIG. 7. However, in other embodiments the resilient member 340 may include two, three, four, five, or more slits. The one or more, or plurality of slits 350 may be adapted to receive a guidewire extending therethrough during a medical procedure, as described later herein.

The slit(s) 350 may extend outward from the circumferential surface 348 of the central opening 346, or the slit(s) 350 may extend outward over another path. For example, the slit(s) 350 may extend radially outward from the circumferential surface 348. In some embodiments, the slit(s) 350 may extend outward in a linear pathway, or the slit(s) 350 may extend outward in a curvilinear fashion. The slit(s) 350 may be configured similar to the slit(s) described in other embodiments disclosed herein.

In some embodiments, such as the embodiment of FIG. 7, the cap 330 may additionally include a guidewire locking structure 360. In some embodiments, the guidewire locking structure 360 may be a unitary portion of the shell 332, whereas in other embodiments, the guidewire locking structure 360 may be a separate component coupled to, secured to, or otherwise brought into association with the cap 330. The guidewire locking structure 360 may be configured to selectively secure a guidewire to the cap 330 for use during a medical procedure. In operation, a desired position of a guidewire may be maintained relative to the endoscope 10 by securing the guidewire with the guidewire locking structure 360.

The guidewire locking structure 360 may include any of a variety of configurations. For example, the guidewire locking structure 360 may include a compliant member 364 located in a channel 362 formed in the sidewall of the shell 332. The compliant member 364 may include a slit 366 extending through the compliant member 364 separating two opposing flaps 368a/368b of the compliant member 364. During operation, a guidewire may be directed into the slit 366 of the compliant member 364 and restrained between the opposing flaps 368a/368b by inward forces imposed by the resiliency of the opposing flaps 368a/368b.

Figure 8:
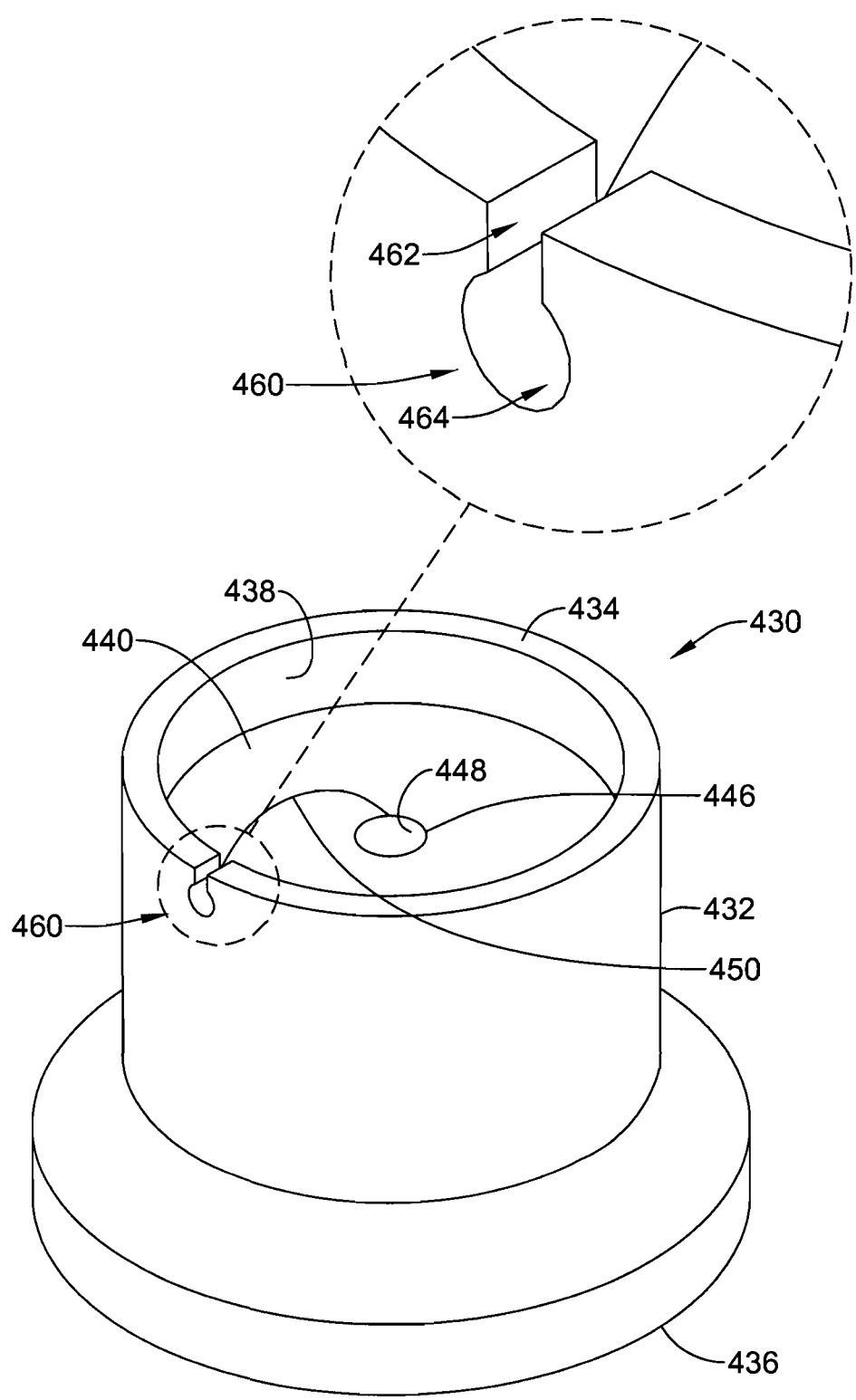
FIG. 8 is another illustrative embodiment of a cap for coupling to an access port of an endoscope.

Another exemplary embodiment of a cap 430 is shown in FIG. 8. The cap 430 may include a relatively rigid outer shell 432 having an upper end 434, a lower end 436 and an inner peripheral surface 438 extending between the upper end 434 and the lower end 436. In some embodiments, the shell 432 may be a generally tubular member having an annular wall.

A resilient member 440 may be positioned interior of the inner peripheral surface 438 of the shell 432. In some embodiments, the resilient member 440 may be formed of a polymeric material, a foam material, or similar material providing the resilient member 440 a degree of resiliency and/or conformability.

The resilient member 440 may be formed of any suitable material. Some suitable materials include polymeric and/or synthetic foams, rubber, silicone and/or elastomers, including thermoelastic polymers such as polyurethane.

In some embodiments, such as the embodiment of FIG. 8, the resilient member 440 may be a generally cylindrical member having an outer circumferential surface. In some embodiments, the outer peripheral surface of the resilient member 440 may be bonded to, adhered to, secured to, engaged with, or otherwise in contact with the inner peripheral surface 438 of the shell 432. The resilient member 440 may include central opening 446 having a circumferential surface 448 extending along the central longitudinal axis of the cap 430 between the upper surface and the lower surface of the resilient member 440.

In some embodiments, the central opening 446 may be cylindrical, conical and/or frusta-conical, or portions may be cylindrical, conical and/or frusta-conical. In some embodiments, such as the embodiment illustrated in FIG. 8, the upper surface of the resilient member 440 may be recessed into the shell 432 below the upper end 434 of the shell 432. However, in some embodiments, the upper surface of the resilient member 440 may extend up to or beyond the upper end 434 of the shell 432.

The resilient member 440 may have a length measured in the direction of the central longitudinal axis of the cap 430, and the shell 432, likewise, may have a length measured in the direction of the central longitudinal axis of the cap 430. In some embodiments, the resilient member 440 may extend a majority, or substantial portion, of the length of the shell 432. In some embodiments, the length of the shell 432 may be in the range of about 2 to about 4 centimeters, whereas the length of the resilient member 440 may be in the range of about 1 to about 3 centimeters. In one embodiment, the length of the shell 432 may be about 3 centimeters, whereas the length of the resilient member 440 may be about 2.6 centimeters. In some embodiments, the length of the resilient member 440 may be 50% or more, 60% or more, 75% or more, or 85% or more of the length of the shell 432. Although some suitable dimensions are disclosed, one of skill in the art, incited by the present disclosure, would understand that desired dimensions may deviate from those expressly disclosed.

The resilient member 440 may also include one or more, or a plurality of slits 450 extending from the circumferential surface 448 of the central opening 446 toward the outer peripheral surface of the resilient member 440. One slit 450 is illustrated in FIG. 8. However, in other embodiments the resilient member 440 may include two, three, four, five, or more slits. The one or more, or plurality of slits 450 may be adapted to receive a guidewire extending therethrough during a medical procedure, as described later herein.

The slit(s) 450 may extend outward from the circumferential surface 448 of the central opening 446, or the slit(s) 450 may extend outward over another path. For example, the slit(s) 450 may extend outward from the circumferential surface 448 in a curvilinear fashion. However, in some embodiments, the slit(s) 450 may extend outward in a linear pathway. The slit(s) 450 may be configured similar to the slit(s) described in other embodiments disclosed herein.

In some embodiments, such as the embodiment of FIG. 8, the cap 430 may additionally include a guidewire locking structure 460. In some embodiments, the guidewire locking structure 460 may be a unitary portion of the shell 432, whereas in other embodiments, the guidewire locking structure 460 may be a separate component coupled to, secured to, or otherwise brought into association with the cap 430. The guidewire locking structure 460 may be configured to selectively secure a guidewire to the cap 430 for use during a medical procedure. In operation, a desired position of a guidewire may be maintained relative to the endoscope 10 by securing the guidewire with the guidewire locking structure 460.

The guidewire locking structure 460 may include any of a variety of configurations. For example, the guidewire locking structure 460 may include a slot 462 providing access to a larger retention area 464 formed in the sidewall of the shell 432. The slot 462, which may be located at the upper surface 434 of the shell 432, may be sized slightly less than the diameter of a guidewire. Thus, a guidewire may be urged through the slot 462 and into the retention area 464, creating a snap fit for the guidewire. As the guidewire is urged through the slot 462, the slot 462 may yield or deflect enough to allow the guidewire to pass through into the retention area 464. The retention area 464 may be of a sufficient size to receive a guidewire. For instance, in some embodiments the opening of the retention area 464 may be sized slightly larger or slightly smaller than the cross-section of a guidewire. Because the slot 462 is sized slightly less than the diameter of a guidewire, the guidewire may not readily pass back through the slot 462 without sufficient urging by an operator.

Figure 9:
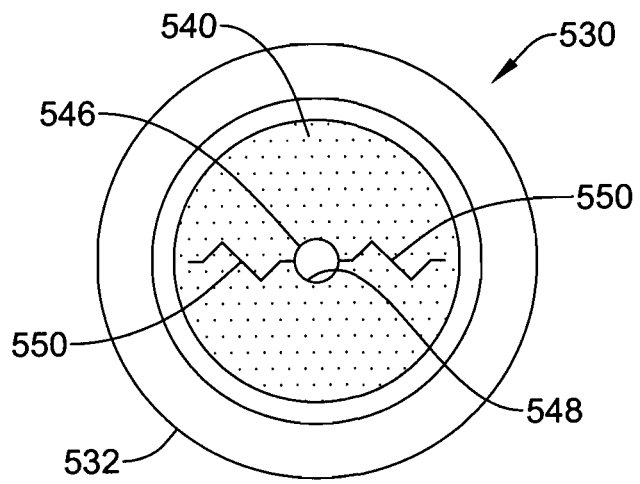
FIG. 9 is a top view of another illustrative embodiment of a cap for coupling to an access port of an endoscope.

Another exemplary embodiment of a cap 530 is shown in FIG. 9. The cap 530 may be similar to the cap 30 illustrated in FIG. 4, with the exception of certain aspects concerning the slits 550 formed in the resilient member 540. Thus, for the sake of repetitiveness, similarities of the cap 530 with those of the cap 30 will not be repeated.

The cap 530 may include a shell 532 encompassing a resilient member 540. The resilient member 540 may include one or more, or a plurality of slits 550. As shown in FIG. 9, the resilient member 540 includes two slits 550 extending in generally opposite directions from a central longitudinal opening 546 extending longitudinally through the resilient member 540. Each of the slits 550 extends generally outward from the circumferential surface 548 of the central opening 546 toward the outer periphery of the resilient member 540. As shown in FIG. 9, each of the slits 550 may extend in a zigzag, back-and-forth, undulating, or angled fashion, or the like.

Figure 10:
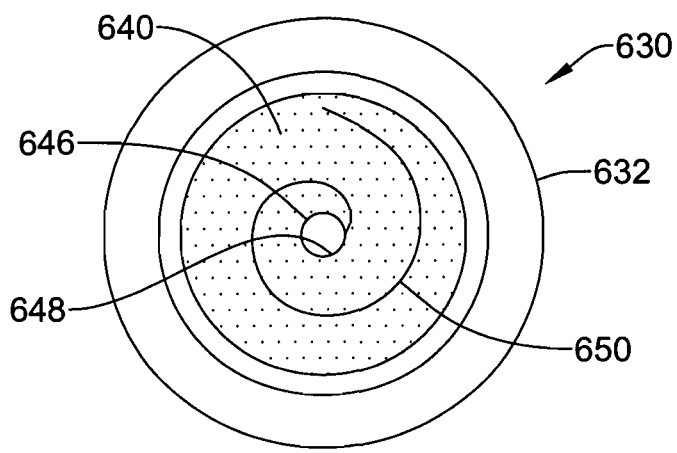
FIG. 10 is a top view of another illustrative embodiment of a cap for coupling to an access port of an endoscope.

Another exemplary embodiment of a cap 630 is shown in FIG. 10. The cap 630 may be similar to the cap 30 illustrated in FIG. 4, with the exception of certain aspects concerning the slit 650 formed in the resilient member 640. Thus, for the sake of repetitiveness, similarities of the cap 630 with those of the cap 30 will not be repeated.

The cap 630 may include a shell 632 encompassing a resilient member 640. The resilient member 640 may include one or more, or a plurality of slits 650. The resilient member 640 includes a slit 650 extending in a generally spiral direction from a central longitudinal opening 646 extending longitudinally through the resilient member 640. The slit 650 extends in a spiral fashion extending generally outward from the circumferential surface 648 of the central opening 646 toward the outer periphery of the resilient member 640.

An exemplary method of using the cap 30 in association with an endoscopic device 90 and a guidewire 95 in order to inhibit the egress of fluids from a working channel of an endoscope during a medical procedure is shown in FIGS. 11A through 11E. In the illustrated embodiment, the endoscopic device 90 is depicted as a catheter including a "U" or "C" channel 92 for receiving the guidewire 95, such as a catheter disclosed in U.S. Pat. No. 6,007,522, incorporated herein by reference. However, in other embodiments, the endoscopic device 90 may be one of several endoscopic devices known in the art. For example, the endoscopic device 90 may be a catheter, sphincterotome, basket, biopsy forceps, snare, or the like.

Figure 11A:
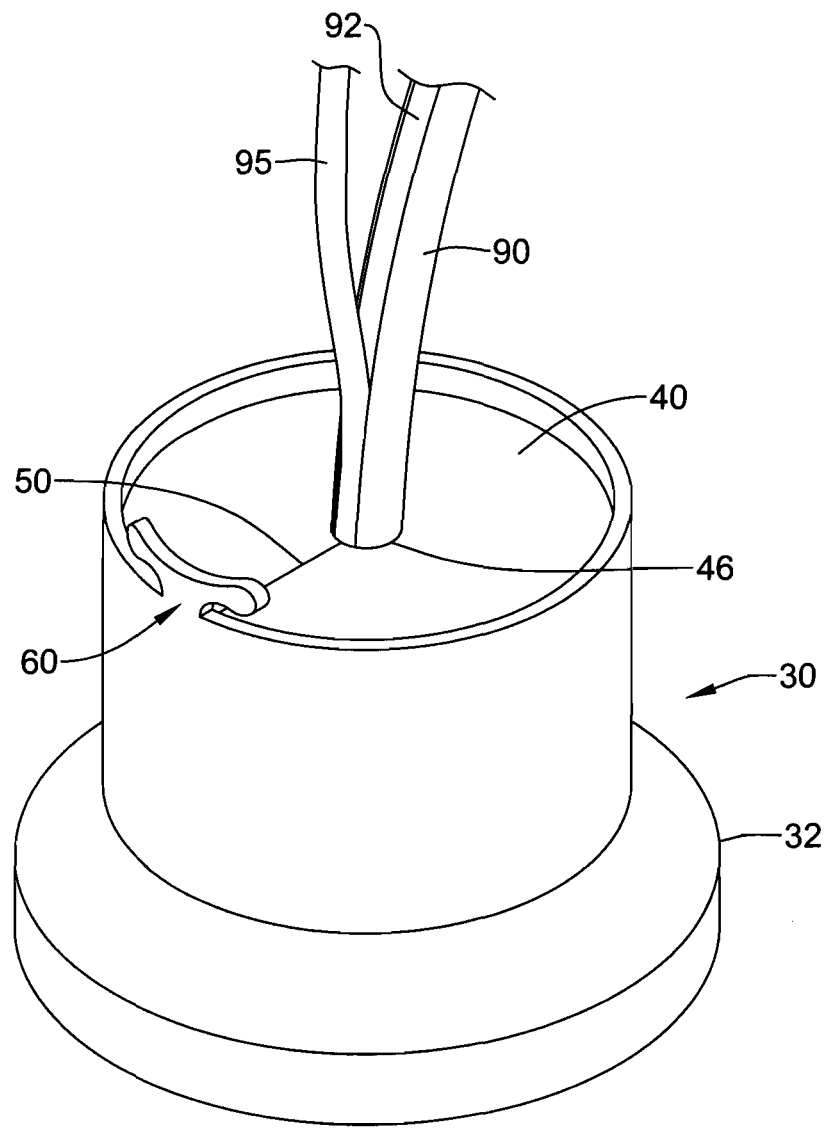
FIG. 11A-11D illustrate a method of using an exemplary cap in association with an endoscopic device and a guidewire.

As shown in FIG. 11A, the endoscopic device 90 may be advanced distally through the central opening 46 of the resilient member 40 such that the endoscopic device 90 is advanced through the working channel of the endoscope (shown in FIG. 1). The endoscopic device 90 may be advanced along a guidewire 95, positioned through the central opening 46 prior to advancing the endoscopic device 90, or the guidewire 95 may be advanced through the cap 30 simultaneously with the endoscopic device 90 or subsequent to advancing the endoscopic device 90 into the working channel through the cap 30. The circumferential surface of the central opening 46, which may be sized to closely approximate the size of the endoscopic device 90, may conform around the circumference of the endoscopic device 90, substantially inhibiting fluid from egressing from the working channel.

Figure 11B:
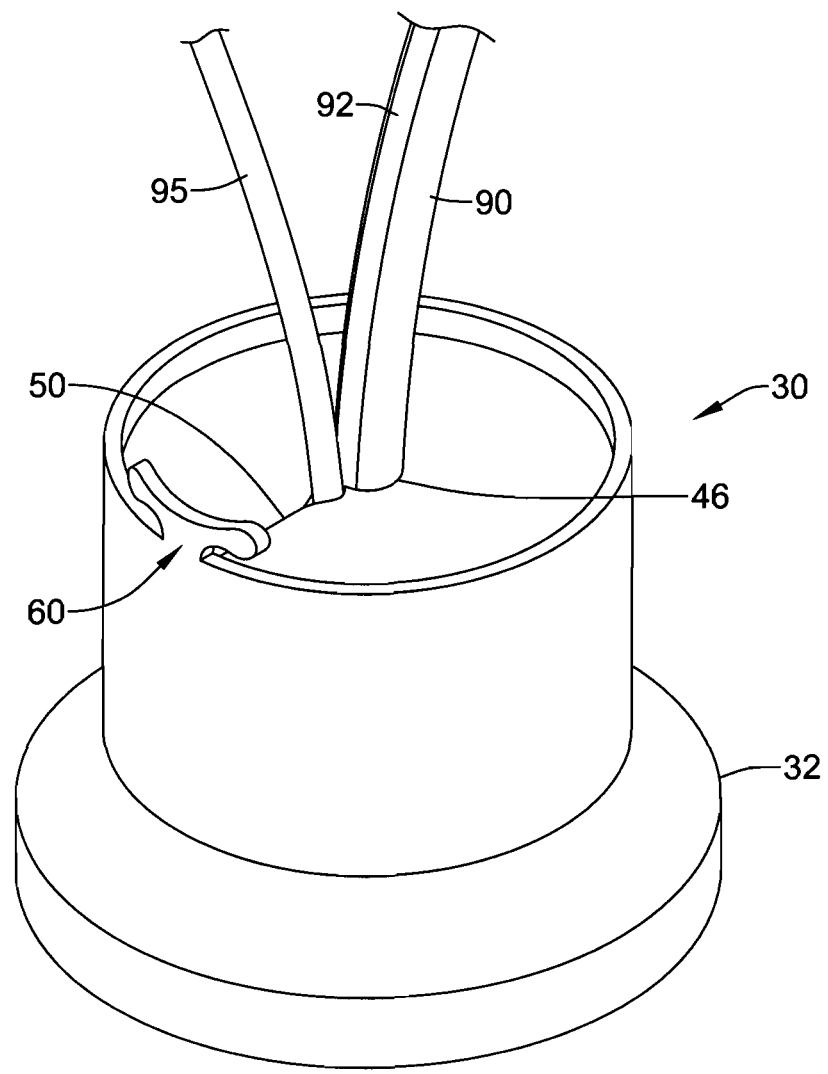

As shown in FIG. 11B, the guidewire 95 may be positioned in the slit 50 along the side of the endoscopic device 90 such that the guidewire 95 extends through the slit 50 at a location radially outward of the circumferential surface of the central opening 46. As the guidewire 95 is positioned in the slit 50, the opposing edges of the slit 50 may conform around the guidewire 95, sufficiently inhibiting any fluid from egressing from the working channel. Correspondingly, the outer circumference of the central opening 46 remains substantially in contact with, or in close association with the entire outer surface of the endoscopic device 90. Thus, while the endoscopic device 90 and the guidewire 95 are extending through the cap 30, substantially no open passageway is formed through the resilient member 40 which would allow fluid to egress from the working channel of an endoscope.

Figure 11C:
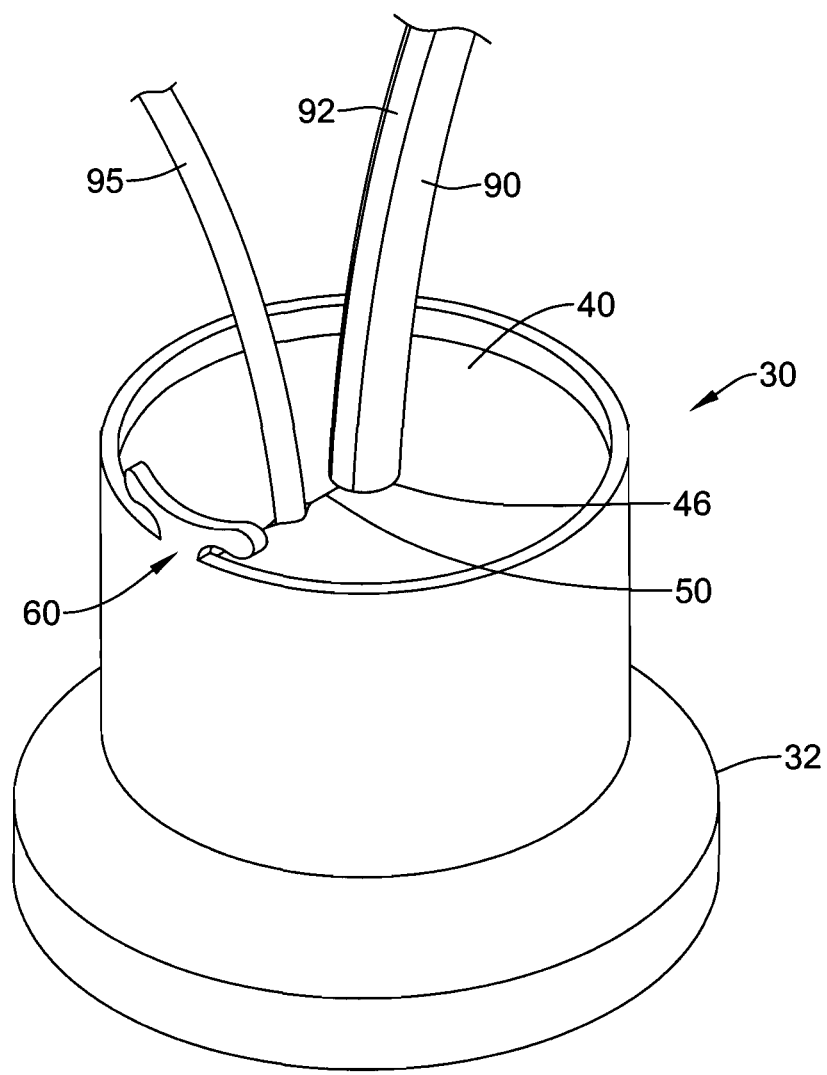

The guidewire 95 may be further drawn away from the endoscopic device, and thus the central longitudinal axis of the cap 30, toward the guidewire locking structure 60, or other peripheral location of the cap 30, as shown in FIG. 11C. As the guidewire 95 is drawn outward from the central longitudinal axis of the cap 30 through the slit 50, the opposing edges of the slit 50 may maintain conformity with the guidewire 95, sufficiently inhibiting any fluid from egressing from the working channel.

Figure 11D:
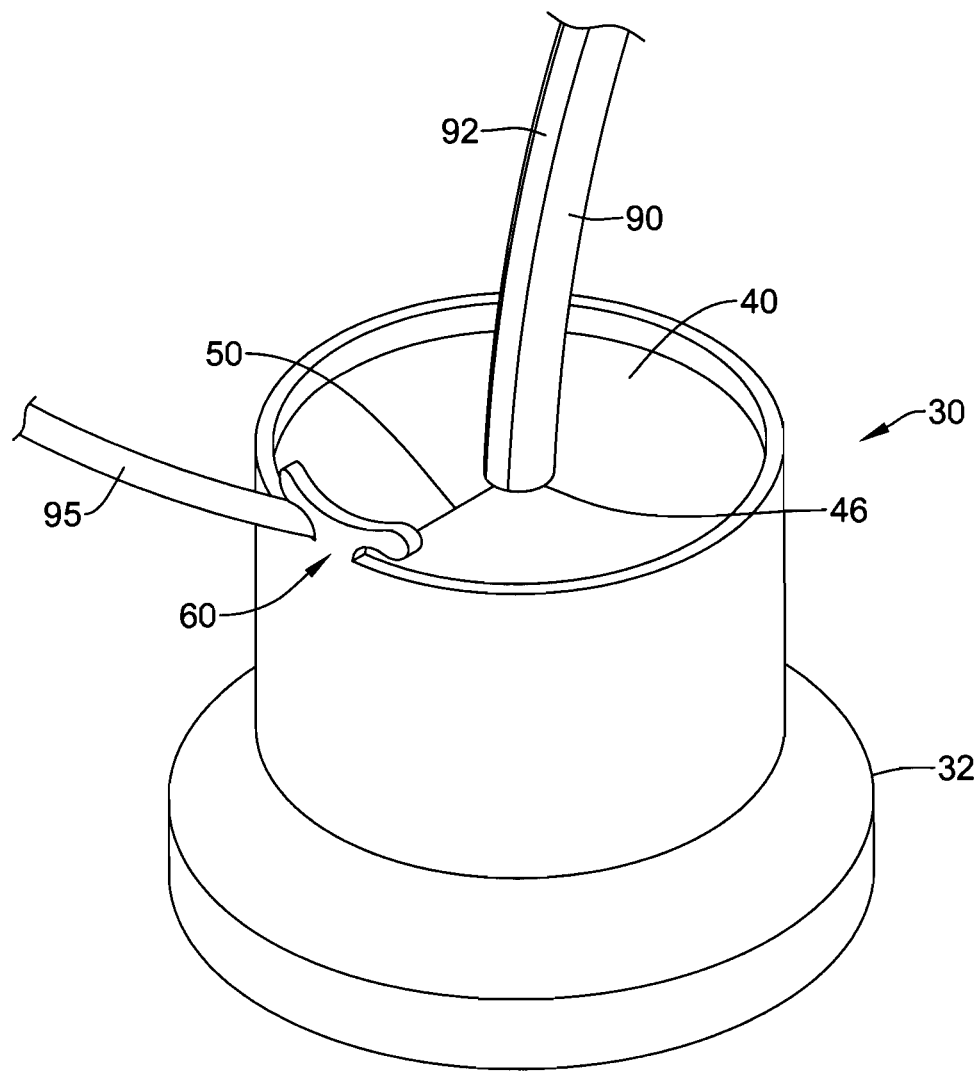

If desired during an endoscopic procedure, the guidewire 95, positioned in the slit 50, may be engaged with the guidewire locking device 60, as shown in FIG. 11D. Thus, the guidewire locking device 60 may be used to prevent further relative longitudinal movement of the guidewire 95 during an endoscopic procedure.

Figure 11E:
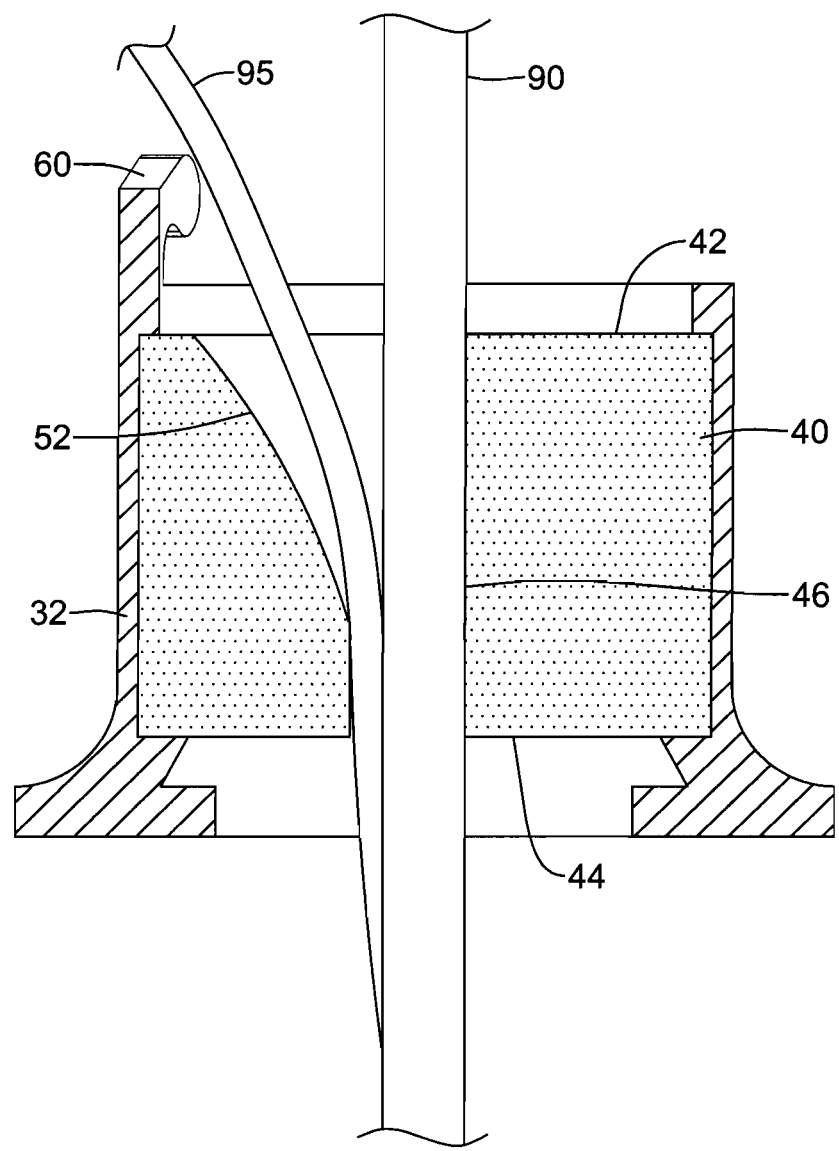
FIG. 11E is a cross-sectional view showing the relative position of an endoscopic device and a guidewire positioned through an exemplary cap.

FIG. 11E is a cross-sectional view showing an exemplary placement of the endoscopic device 90 and the guidewire 95 through the cap 30. As shown in FIG. 11E, the endoscopic device 90 may be sufficiently retained through the central longitudinal opening 46, while the guidewire 95 may be positioned through the slit 50, directed outward from the central longitudinal opening 46 toward the outer edge 52 of the slit 50. In such an embodiment, there may be substantially no open passageway through the resilient member 40 allowing fluid to egress from the working channel of an endoscope.

In embodiments in which multiple guidewires are desired, the first guidewire 95 may be positioned through the slit 50, directed outward from the central longitudinal opening 46 toward the outer edge 52 of the slit 50. A second or additional guidewire may be positioned through the slit 50, or another slit, directed outward from the central longitudinal opening 46 toward the outer edge 52 of the slit 50.

In embodiments in which the resilient member 40 includes a plurality of slits 50, an additional guidewire 95 may be similarly positioned through the second or additional slit 50, such that the second or additional guidewire extends through a second or additional slit 50 at a location radially outward of the circumferential surface 48 of the central opening 46.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A cap for inhibiting egress of fluid from an access port of an endoscope working channel, the cap comprising:

an outer shell removable from the access port, the outer shell including an upper end, a lower end, an outer peripheral surface extending from the upper end to the lower end, and an inner peripheral surface extending from the upper end to the lower end, the inner peripheral surface extending about a central longitudinal axis of the outer shell, the outer shell further including a coupling portion proximate the lower end of the outer shell adapted for coupling the cap to an endoscope; and a single resilient member positioned interior of the inner peripheral surface of the outer shell, the resilient member including an upper surface, a lower surface, an outer peripheral surface extending between the upper surface and the lower surface, and a central cylindrical opening defined in the resilient member that is sized to accommodate an endoscopic instrument therethrough, the central opening having a circumferential surface extending between the upper surface and the lower surface of the resilient member, wherein the central cylindrical opening has a constant diameter between the upper surface and the lower surface, the resilient member further including a slit extending outward from the circumferential surface of the central opening toward the outer peripheral surface of the resilient member; and a guidewire locking structure formed by two tabs opposing one another, each tab extending from and above the upper end of the outer shell forming an opening between each respective tab and the upper end;

wherein the slit extends further outward from the longitudinal axis at a location proximate the upper surface of the resilient member than at a location proximate the lower surface of the resilient member.

2. The cap of claim 1, wherein the slit extends spirally outward.

3. The cap of claim 1, wherein the slit extends outward in a zigzag fashion.

4. The cap of claim 1, wherein the slit extends radially outward.

5. The cap of claim 4, further comprising a second slit extending radially outward from the circumferential surface of the central opening toward the outer peripheral surface of the resilient member.

6. The cap of claim 5, wherein second slit is located less than 90 degrees from the slit.

7. The cap of claim 5, wherein the second slit is located about 5 to about 30 degrees from the slit.

8. The cap of claim 5, wherein the second slit is located about 10 to about 15 degrees from the slit.

9. The cap of claim 1, wherein the outer shell further includes a guidewire locking structure.

10. The cap of claim 1, wherein the resilient member is formed of a polymeric material.

11. The cap of claim 1, wherein the coupling portion includes a threaded portion.

12. The cap of claim 1, wherein the coupling portion includes a compliant member.

13. The cap of claim 1, wherein the coupling portion includes a groove.

14. The cap of claim 1, wherein the coupling portion includes a lip.

* * * * *